United States Patent
May et al.

(10) Patent No.: US 11,627,954 B2
(45) Date of Patent: Apr. 18, 2023

(54) BI-PLANAR INSTRUMENT FOR BONE CUTTING AND JOINT REALIGNMENT PROCEDURE

(71) Applicant: Treace Medical Concepts, Inc., Ponte Vedra, FL (US)

(72) Inventors: Jason May, St. John's, FL (US); Robert D. Santrock, Morgantown, WV (US); Sean F. Scanlan, Jacksonville, FL (US); John T. Treace, Ponte Vedra Beach, FL (US); Joe W. Ferguson, Ponte Vedra Beach, FL (US); Jody McAleer, Jefferson City, MO (US); Daniel J. Hatch, Greeley, CO (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

(21) Appl. No.: 16/987,916

(22) Filed: Aug. 7, 2020

(65) Prior Publication Data
US 2021/0038212 A1  Feb. 11, 2021

Related U.S. Application Data

(60) Provisional application No. 62/883,649, filed on Aug. 7, 2019.

(51) Int. Cl.
*A61B 17/56* (2006.01)
*A61B 17/02* (2006.01)
(Continued)

(52) U.S. Cl.
CPC ........ *A61B 17/025* (2013.01); *A61B 17/1775* (2016.11); *A61B 2017/00473* (2013.01); *A61B 2017/564* (2013.01)

(58) Field of Classification Search
CPC ..... A61B 17/02; A61B 17/025; A61B 17/151; A61B 17/8866; A61B 2017/00473; A61B 2017/564; A61B 2017/565
See application file for complete search history.

(56) References Cited

U.S. PATENT DOCUMENTS

| 3,664,022 A | 5/1972 | Small |
| 4,069,824 A | 1/1978 | Weinstock |

(Continued)

FOREIGN PATENT DOCUMENTS

| AU | 2009227957 B2 | 7/2014 |
| CA | 2491824 A1 | 9/2005 |

(Continued)

OTHER PUBLICATIONS

"Accu-Cut Osteotomy Guide System," BioPro, Brochure, Oct. 2018, 2 pages.

(Continued)

*Primary Examiner* — Samuel S Hanna
(74) *Attorney, Agent, or Firm* — Fredrikson & Byron, P.A.

(57) ABSTRACT

A technique for correcting a bone deformity, such as a bunion, may be performed using an instrument that defines a spacer body connected to a fulcrum. The spacer body portion of the instrument can be inserted into a joint space between opposed bone ends. The fulcrum body can be inserted between adjacent metatarsals. An angle set between the spacer body and fulcrum body can help properly position both features within different joint spaces for ensuring that subsequent steps of the surgical procedure are properly performed and instrumentation is appropriately aligned.

21 Claims, 16 Drawing Sheets

(51) Int. Cl.
*A61B 17/17* (2006.01)
*A61B 17/00* (2006.01)

(56) References Cited

U.S. PATENT DOCUMENTS

| | | |
|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 7,018,383 B2 | 3/2006 | McGuire |
| 7,033,361 B2 | 4/2006 | Collazo |
| 7,097,647 B2 | 8/2006 | Segler et al. |
| 7,112,204 B2 | 9/2006 | Justin et al. |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Buescher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,518,045 B2 | 8/2013 | Szanto |
| 8,523,870 B2 | 9/2013 | Green, II et al. |
| 8,529,571 B2 | 9/2013 | Horan et al. |

(56) References Cited

U.S. PATENT DOCUMENTS

| | | |
|---|---|---|
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassy et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,452,057 B2 | 9/2016 | DaCosta et al. |
| 9,522,023 B2 | 11/2016 | Haddad et al. |
| 9,592,084 B2 | 3/2017 | Grant |
| 9,750,538 B2 | 9/2017 | Soffiatti et al. |
| 9,785,747 B2 | 10/2017 | Geebelen |
| 9,980,760 B2 | 5/2018 | DaCosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,856,886 B2 | 12/2020 | Dacosta et al. |
| 10,856,918 B2 | 12/2020 | Dacosta |
| 10,939,939 B1 | 3/2021 | Gil et al. |
| 11,304,705 B2 | 4/2022 | Fallin et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0267482 A1 | 12/2005 | Hyde, Jr. |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |

(56) References Cited

U.S. PATENT DOCUMENTS

| | | |
|---|---|---|
| 2013/0035694 A1 | 2/2013 | Grimm et al. |
| 2013/0085499 A1 | 4/2013 | Lian |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | DaCosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton |
| 2016/0022315 A1 | 1/2016 | Soffiatti et al. |
| 2016/0135858 A1 | 5/2016 | DaCosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0192970 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0014143 A1 | 1/2017 | Dayton et al. |
| 2017/0014173 A1 | 1/2017 | Smith et al. |
| 2017/0042598 A1 | 2/2017 | Santrock et al. |
| 2017/0042599 A1 | 2/2017 | Bays et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2017/0172638 A1* | 6/2017 | Santrock ............ A61B 17/8866 |
| 2018/0132868 A1 | 5/2018 | Dacosta et al. |
| 2018/0289379 A1 | 10/2018 | Dacosta et al. |
| 2018/0344334 A1 | 12/2018 | Kim et al. |
| 2020/0015874 A1 | 1/2020 | Hartson et al. |
| 2020/0229828 A1 | 7/2020 | Wagner et al. |
| 2020/0237387 A1 | 7/2020 | Luttrell et al. |
| 2020/0330109 A1 | 10/2020 | Woodard et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 103735306 A | 4/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | S635739 A | 1/1988 |
| JP | H0531116 A | 2/1993 |
| JP | 2004174265 A | 6/2004 |
| JP | 2006158972 A | 6/2006 |

(56) References Cited

FOREIGN PATENT DOCUMENTS

| | | |
|---|---|---|
| JP | 4134243 B2 | 8/2008 |
| JP | 2008537498 A | 9/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |
| WO | 2020180598 A1 | 9/2020 |

OTHER PUBLICATIONS

"Acumed Osteotomiesystem Operationstechnik," Acumed, 2014, 19 pages (including 3 pages English translation).
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).
Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Coetzee et al., "The Lapidus Procedure: A Prospective Cohort Outcome Study," Foot & Ankle International, vol. 25, No. 8, Aug. 2004, pp. 526-531.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
"Futura Forefoot Implant Arthroplasty Products," Tornier, Inc., 2008, 14 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online Nov. 21, 2014, pp. 437-440.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"HAT-TRICK Lesser Toe Repair System," Smith & Nephew, Brochure, Aug. 2014, 12 pages.
"HAT-TRICK Lesser Toe Repair System, Foot and Ankle Technique Guide, Metatarsal Shortening Osteotomy Surgical Technique," Smith & Nephew, 2014, 16 pages.

(56) References Cited

OTHER PUBLICATIONS

Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Mortier et al., "Axial Rotation of the First Metatarsal Head in a Normal Population and Hallux Valgus Patients," Orthopaedics and Traumatology: Surgery and Research, vol. 98, 2012, pp. 677-683.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
Lapidus, "The Author's Bunion Operation From 1931 to 1959," Clinical Orthopaedics, vol. 16, 1960, pp. 119-135.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
International Patent Application No. PCT/US2020/045393, International Search Report and Written Opinion dated Nov. 20, 2020, 10 pages.
Nagy et al., "The AO Ulnar Shortening Osteotomy System Indications and Surgical Technique," Journal of Wrist Surgery, vol. 3, No. 2, 2014, pp. 91-97.

NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Smith & Nephew scores a HAT-TRICK with its entry into the high-growth hammer toe repair market," Smith & Nephew, Jul. 31, 2014, 2 pages.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Talbot et al., "Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.

(56) References Cited

OTHER PUBLICATIONS

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fußchirurgie Das V-tek-System," ABW Wissenschaftsverlag GmbH, 2009, 11 pages, including English Abstract.

Weber et al., "A Simple System For Navigation Of Bone Alignment Osteotomies Of The Tibia," International Congress Series, vol. 1268, Jan. 2004, pp. 608-613, (Abstract Only).

Weil et al., "Anatomic Plantar Plate Repair Using the Weil Metatarsal Osteotomy Approach," Foot & Ankle Specialist, vol. 4, No. 3, 2011, pp. 145-150.

Wendl et al., "Navigation in der Knieendoprothetik," OP-Journal, vol. 17, 2002, pp. 22-27, including English Abstract.

Whipple et al., "Zimmer Herbert Whipple Bone Screw System: Surgical Techniques for Fixation of Scaphoid and Other Small Bone Fractures," Zimmer, 2003, 59 pages.

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

Yasuda et al., "Proximal Supination Osteotomy of the First Metatarsal for Hallux Valgus," Foot and Ankle International, vol. 36, No. 6, Jun. 2015, pp. 696-704.

Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.

Conti et al., "Effect of the Modified Lapidus Procedure on Pronation of the First Ray in Hallux Valgus," Foot & Ankle International, Feb. 1, 2020, published online: Oct. 16, 2019, 8 pages.

Conti et al., "Effect of the Modified Lapidus Procedure for Hallux Valgus on Foot Width," Foot & Ankle International, Feb. 1, 2020, published online: Oct. 30, 2019, 6 pages.

Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.

Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.

Hatch et al., "Triplane Hallux Abducto Valgus Classification," The Journal of Foot & Ankle Surgery, vol. 57, No. 5, Sep./Oct. 2018, published online: May 18, 2018, pp. 972-981.

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online Dec. 26, 2019, pp. 426-436.

Li et al., "Evolution of Thinking of the Lapidus Procedure and Fixation," Foot and Ankle Clinics, vol. 25, No. 1, Mar. 2020, published online: Dec. 16, 2019, pp. 18 pages.

Lopez et al., "Metatarsalgia: Assessment Algorithm and Decision Making," Foot and Ankle Clinics, vol. 24, No. 4, Dec. 2019, published online: Sep. 25, 2019, pp. 561-569.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

Walker et al., "The Role of First Ray Insufficiency in the Development of Metatarsalgia," Foot and Ankle Clinics, vol. 24, No. 4, Dec. 2019, published online: Sep. 5, 2019, pp. 641-648.

Claim Chart for Groves Public use (Mar. 26, 2014), Exhibit B4 of Defendant Fusion Orthopedics LLC's Invalidity Contentions, No. CV-22-00490-PHX-SRB, U.S. District Court for the District of Arizona, Aug. 27, 2022, 161 pages.

Groves, "Operative Report," St. Tammany Parish Hospital, Date of Procedure, Mar. 26, 2014, 2 pages.

D'Amico et al., "Motion of the First Ray: Clarification Through Investigation," Journal of the American Podiatry Association, vol. 69, No. 1, Jan. 1979, pp. 17-23.

Okuda et al., "Proximal Metatarsal Ostetomy for Hallux Valgus: Comparison of Outcome for Moderate and Server Deformities," Foot and Ankle International, vol. 29, No. 7, Jul. 2008, pp. 664-670.

Okuda et al., "The Shape of the Lateral Edge of the First Metatarsal Head as a Risk Factor for Recurrence of Hallux Valgus," Journal of Bone and Joint Surgery, vol. 89, 2007, pp. 2163-2172.

Mizuno et al., "Detorsion Osteotomy of the First Metatarsal Bone in Hallux Valgus," Japanese Orthopaedic Association, Tokyo, 1956; 30:813-819.

Eustace et al., "Hallux valgus, first metarsal pronation and collapse of the medical longitudinal arch—a radiological correlation," Skeletal Radiology, vol. 23, 1994, pp. 191-194.

Collan et al., "The biomechanics of the first metatarsal bone in hallux valgus: A preliminary study utilizing a weight bearing extremity CT," Foot and Ankle Surgery, vol. 19, 2013, pp. 155-161.

Le et al., "Tarsometatrsal Arthrodesis," Operative Techniques in Foot and Ankle Surgery, Section II, Chapter 40, 2011, pp. 281-285.

Coetzee et al., "Revision Hallux Valgus Correction," Operative Techniques in Foot and Ankle Surgery, Section I, Chapter 15, 2011, pp. 84-96.

"Foot and Ankle Instrument Set," Smith & Nephew, 2013, 2 pages.

"Lapidus Pearls: Gaining Joint Exposure to Decrease Non-Union," Youtube, Retrieved online from <https://www.youtube.com/watch?v=jqJyE7pj-Y>, dated Nov. 2, 2009, 3 pages.

"Reconstructive Surgery of the Foot & Ankle," The Podiatry Institute, Update 2015, Conference Program, May 2015, 28 pages.

"Speed Continuous Active Compressino Implant," BioMedical Enterprises, Inc., A120-029 Rev. 3, 2013, 4 pages.

"Visionaire: Patient Matched Cutting Blocks Surgical Procedure," Smith & Nephew, Inc., 2009, 2 pages.

Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.

Baravarian, "Why the Lapidus Procedure is Ideal for Bunions," Podiatry Today, Retrieved online from <https://www.hmpgloballearthmpgloballe.com/site/podipodi/article/5542>, dated May 2006, 8 pages.

Bauer et al., "Offset-V Ostetomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.

Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.

Coughlin, "Fixation of the Lapidus Arthrodesis with a Plantar Interfragmentary Screw and Medial Low Profile Locking Plate," Orthopaedics and Traumatology, vol. 7, 1999, pp. 133-143.

Dayton et al., "Observed Changes in Radiographic Measurements of the First Ray after Frontal Plante Rotation of the First Metatarsal in a Cadaveric Foot Model," The Journal of Foot & Ankle Surgery, vol. 53, 2014, pp. 274-278.

Dayton et al., "Relationship of Frontal Plante Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Artical in Press, Mar. 1, 2013, 7 pages.

DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.

Fallin et al., U.S. Provisional Application entitled Indexed Tri-Planar Osteotomy Guide and Method, U.S. Appl. No. 62/118,378, filed Feb. 19, 2015, 62 pages.

Fishco, "A Straightforward Guide To The Lapidus Bunionectomy,"Podiatry Today, Retrieved online from <https://www.hmpgloballearningnetwork.com/site/podiatry/blogged/straightforward-guide-lapidus-bunionectomy>, dated Sep. 6, 2013, 5 pages.

(56) References Cited

OTHER PUBLICATIONS

Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthpedics, vol. 31, No. 3, Mar. 2008, 7 pages.
Giannoudis et al., "Hallux Valgus Correction," Practical Procedures in Elective Orthpaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a paitent focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Mote et al., "First Metarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Ostetomy for Correction of Moderate and Sever Hallux Valgus Deformity," Foot & Ankle International, vol. 28, No. 7, Jul. 2007, pp. 857-864.
Schon et al., "Cuneiform-Metatarsal Arthrodesis for Hallux Valgus,"The Foot and Ankle, Second Edition, Chapter 8, 2002, pp. 99-117.
Sokoloff, "Lapidus Procedure," Textbook of Bunion Surgery Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatrarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation For Nonunions: What the Evidence Reveals," Podiatry Today, vol. 24, No. 9, Sep. 2011, pp. 52-57.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journalp of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plante Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014,, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in Bunion Deformity?, " The Journal of Foot and Ankle Surgery, Article in Press, 2014, 4 pages.
Rodgriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," Foot and Ankle Specialist, 2014, 3 pages.

(56) References Cited

OTHER PUBLICATIONS

Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?, " Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vo. 51, 2012, pp. 50-56.
Easley et al., "Current Concepts Review: Hallux Valgus Part I: Pathomechancis, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Asses Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?, " Evidence-Based Orthopaedics—The Best Answers to Clinical Questions, Chapter 73, 2009, 479-491.
Shurnas et al., "Proximal Metatarsal Opening Wedge Osteotomy," Operative Techniques in Foot and Ankle Surgery, Section I, Chapter 13, 2011, pp. 73-78.
Defendant Fusion Orthopedics LLC's Invalidity Contentions, No. CV-22-00490-PHX-SRB, U.S. District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, U.S. District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, U.S. District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, U.S. District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions No. CV-22-00490-PHX-SRB, U.S. District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, U.S. District Court for the District of Arizona, Aug. 27, 2022, 21 pages.
Claim Chart for U.S. Pat. No. 10,376,268 to Fallin et al., entitled "Indexed Tri-Planar Ostetomy Guide and Method," Issued Aug. 13, 2019, Exhibit B6 of Defendant Fusion Orthopedics LLC's Invalidity Contentions, No. CV-22-00490-PHX-SRB, U.S. District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, U.S. District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, U.S. District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, U.S. District for the District of Arizona, Aug. 27, 2022, 153 pages.

\* cited by examiner

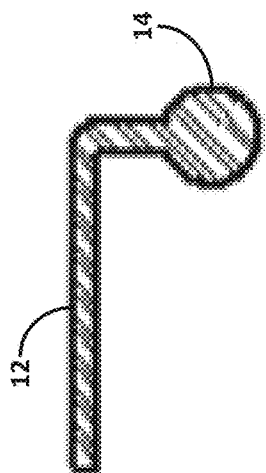
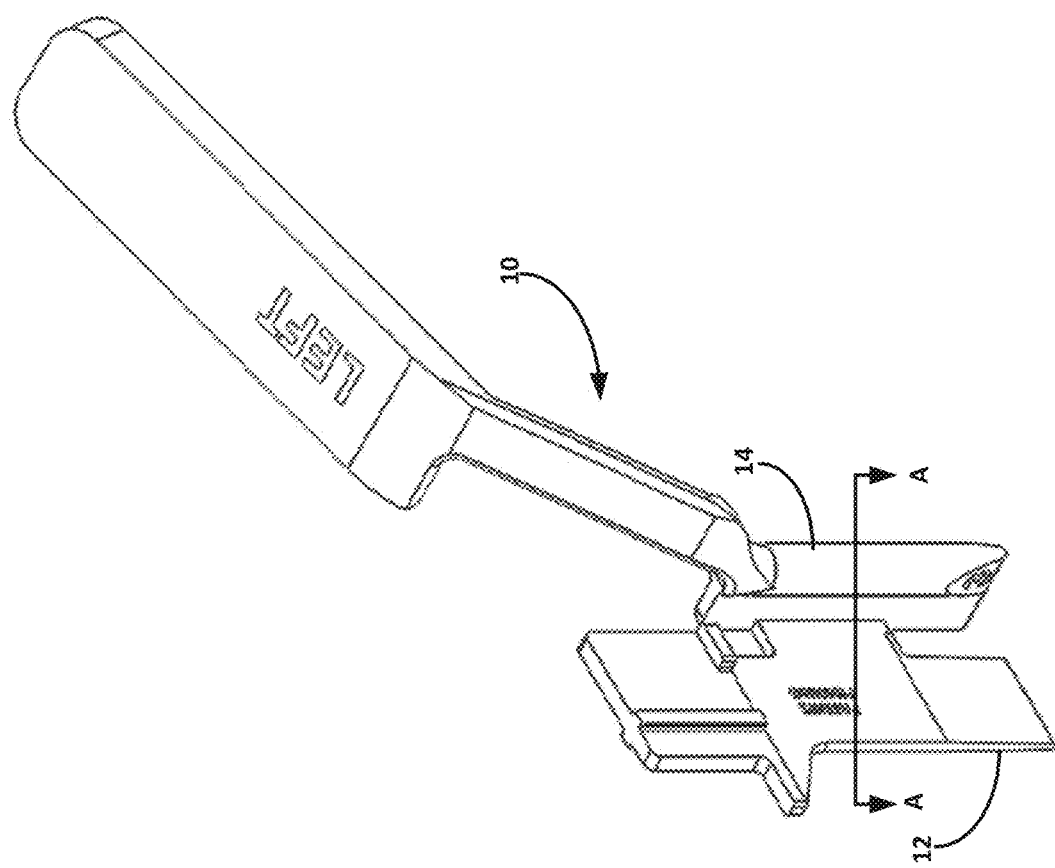
FIG. 5F
FIG. 5E

BI-PLANAR INSTRUMENT FOR BONE CUTTING AND JOINT REALIGNMENT PROCEDURE

CROSS-REFERENCE

This application claims the benefit of U.S. Provisional Patent Application No. 62/883,649, filed Aug. 7, 2019, the entire contents of which are incorporated herein by reference.

TECHNICAL FIELD

This disclosure relates to surgical devices and, more particularly, to surgical devices for assisting in bone cutting and/or realignment techniques.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is medially deviated, resulting in an abduction of the first metatarsal while the phalanges adduct. This often leads to development of soft tissue and a bony prominence on the medial side of the foot, which is called a bunion.

Surgical intervention may be used to correct a bunion deformity. A variety of different surgical procedures exist to correct bunion deformities and may involve removing the abnormal bony enlargement on the first metatarsal and/or attempting to realign the first metatarsal relative to the adjacent metatarsal. Surgical instruments that can facilitate efficient, accurate, and reproducible clinical results are useful for practitioners performing bone realignment techniques.

SUMMARY

In general, this disclosure is directed to an instrument that can be used in a surgical bone cutting and/or realignment procedure. The instrument can include a spacer body connected to a fulcrum body. The spacer body and fulcrum body may be positionable in adjacent joint spaces, with a connecting member between the spacer body and fulcrum body helping to control the relative position of the spacer body and fulcrum body when inserted into respective joint spaces.

For example, the spacer body can be positioned in a joint space between opposed bone ends, such as a joint space between a metatarsal and an opposed cuneiform. In some implementations, the metatarsal is a first metatarsal and the opposed cuneiform is a medial cuneiform. In either case, the spacer body may define a first portion positionable in the joint space between opposed bone ends and a second portion that extends above (e.g., dorsally) from the joint space. The second portion of the spacer body can be connected to a bone preparation guide. The bone preparation guide may be removable from and engageable with the spacer body (e.g., by inserting the bone preparation guide on the spacer body after the spacer body is inserted into the joint space). Alternatively, the bone preparation guide can be permanently coupled to the spacer body (e.g., to define a unitary structure). In either case, the bone preparation guide may define one or more guide surfaces for guiding a bone preparation instrument to prepare the ends of adjacent bones (e.g., to prepare an end of the metatarsal and/or an end of the opposed cuneiform). For example, the bone preparation guide may define at least one cutting slot positioned over the metatarsal for guiding a saw blade to cut an end of the metatarsal and at least one cutting slot positioned over the opposed cuneiform for guiding a saw blade to cut an end of the opposed cuneiform.

The instrument also includes a fulcrum body coupled to the spacer body. The fulcrum body may be configured (e.g., sized and/or shaped) to be positioned in an intermetatarsal space between adjacent metatarsals, such as in the intermetatarsal space between the first metatarsal and the second metatarsal. The fulcrum body may define a fulcrum, or pivot surface, about which the metatarsal can rotate to realign a position of the metatarsal relative to the opposing cuneiform and/or adjacent metatarsal. For example, the fulcrum body may define a pivot surface about which a proximal base of the metatarsal can pivot as an intermetatarsal angle is closed between the metatarsal and the adjacent metatarsal. This may help prevent the base of the metatarsal from shifting laterally, such as by compressing against the adjacent metatarsal, as the metatarsal is realigned.

In some configurations, the spacer body is coupled to the fulcrum body with a bridge member. The bridge member may transition from one plane (e.g., generally in the frontal plane) in which the spacer body is positioned to a second plane (e.g., generally in the sagittal plane) in which the fulcrum body is positioned. For example, the bridge member may define a corner (e.g., with an interior angle ranging from 60 degrees to 120 degrees, such as from 80 degrees to 100 degrees, or approximately 90 degrees) operatively connecting the spacer body to the fulcrum body. In use, the bridge member can be positioned against a corner of the metatarsal being realigned, such as a proximal-lateral corner/surface of the metatarsal. When so positioned, the spacer body may be positioned in the joint space between the metatarsal and opposed cuneiform while the fulcrum body may be positioned in the joint space between the metatarsal and adjacent metatarsal. The bridge member may help establish a fixed position between the spacer body and fulcrum body and/or prevent the spacer body and fulcrum body from shifting relative to each other and/or in their respective joint spaces during the surgical procedure. This can help ensure that the spacer body and fulcrum body are appropriately positioned for subsequent procedure steps performed using the spacer body and fulcrum body (e.g., performing a bone preparation step using a bone preparation guide attached to the spacer body and/or realigning a metatarsal by pivoting about the fulcrum body).

In one example, a bi-planar instrument for a bone cutting and joint realignment procedure is described. The instrument includes a spacer body configured to be inserted into a joint space between a metatarsal and an opposed cuneiform of a foot. The instrument also includes a fulcrum body coupled to the spacer body, the fulcrum body being configured to be inserted in an intermetatarsal space between the metatarsal and an adjacent metatarsal.

In another example, a method is described that includes inserting a spacer body into a joint space between a metatarsal and an opposed cuneiform of a foot. The method also includes inserting a fulcrum body coupled to the spacer between the metatarsal and an adjacent metatarsal. The method further involves preparing an end of the metatarsal using a bone preparation guide aligned with the spacer to guide a bone preparation instrument and preparing an end of the opposing cuneiform using the bone preparation guide to guide a bone preparation instrument. In addition, the method includes moving the metatarsal relative to the adjacent metatarsal in at least a transverse plane, thereby pivoting the metatarsal about the fulcrum body and reducing an intermetatarsal angle between the metatarsal and the adjacent metatarsal.

The details of one or more examples are set forth in the accompanying drawings and the description below. Other features, objects, and advantages will be apparent from the description and drawings, and from the claims.

BRIEF DESCRIPTION OF DRAWINGS

FIGS. 5E and 5F are perspective and sectional views, respectively, showing an example configuration of a fulcrum body defining a convex bone contacting surface.

DETAILED DESCRIPTION

In general, the present disclosure is directed to an instrument that includes a spacer body and fulcrum body that can be used in a surgical procedure, such as bone realignment procedure. Example procedures in which the fulcrum structures may be used include a bone alignment, osteotomy, fusion procedure, and/or other procedures where one or more bones are operated upon and/or realigned relative to one or more bones. Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing an instrument that includes two bodies joined together by a bridge member can be performed to correct an alignment between a metatarsal (e.g., a first metatarsal) and a second metatarsal and/or a cuneiform (e.g., a medial, or first, cuneiform), such as in a bunion correction surgery. An example of such a procedure is a Lapidus procedure (also known as a first tarsal-metatarsal fusion). While the example instruments of the disclosure are generally described as being useful for insertion into a space between opposed bone ends transitioning into an intermetatarsal space, the instruments may be used in any desired application and the disclosure is not limited in this respect.

Figure 1B:
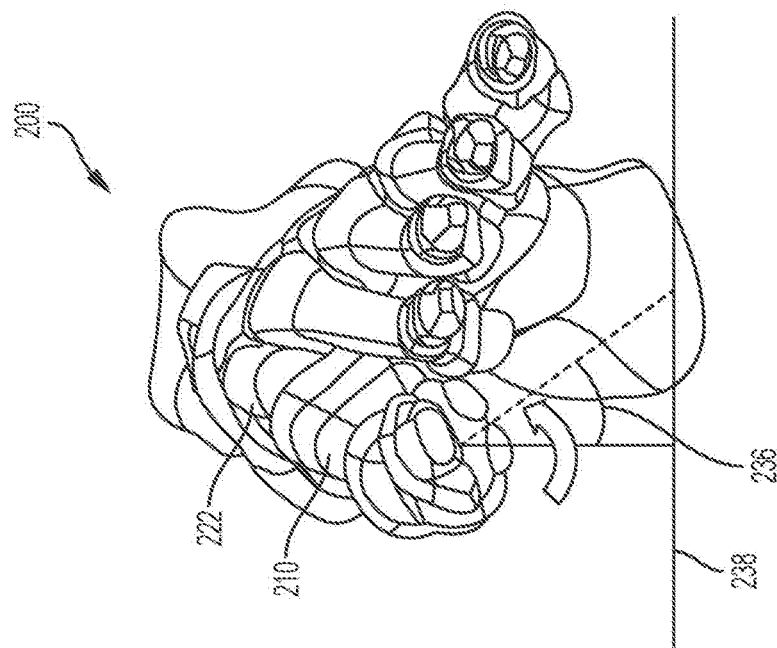
FIGS. 1A and 1B are front views of a foot showing a normal first metatarsal position and an example frontal plane rotational misalignment position, respectively.
Figure 1A:
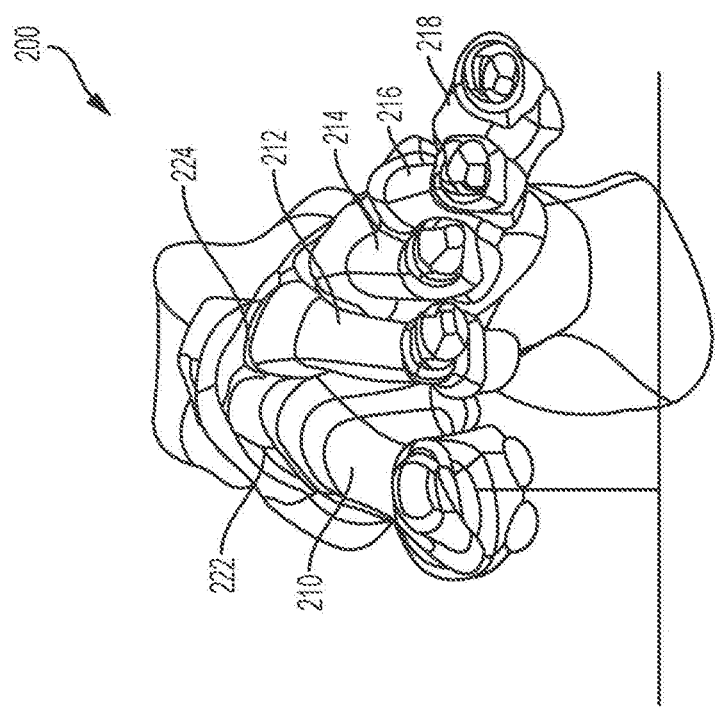
Figure 2B:
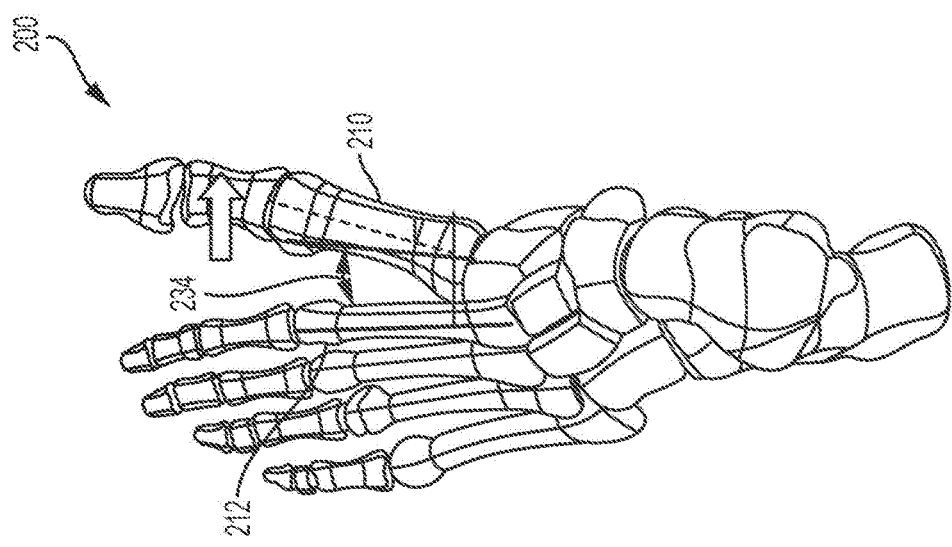
FIGS. 2A and 2B are top views of a foot showing a normal first metatarsal position and an example transverse plane misalignment position, respectively.
Figure 2A:
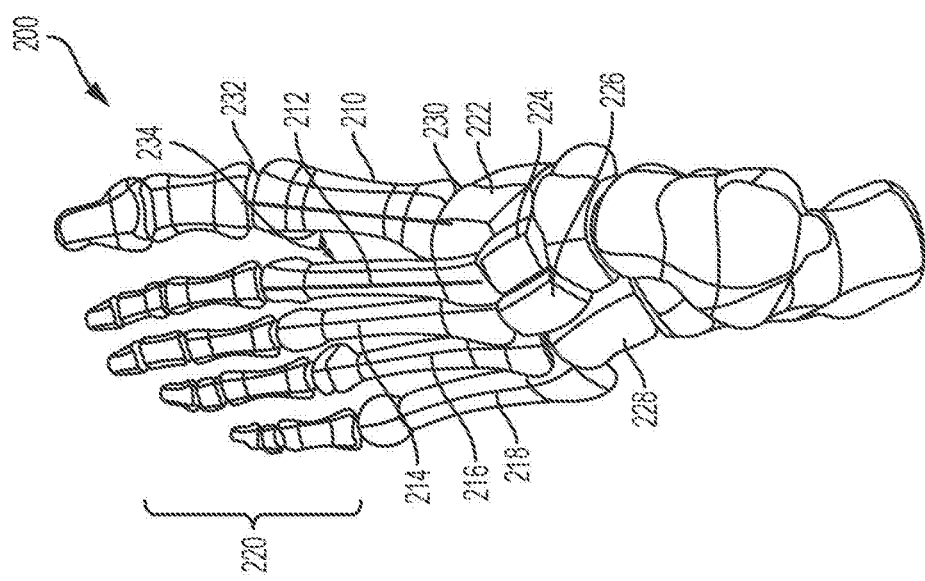
Figure 3B:
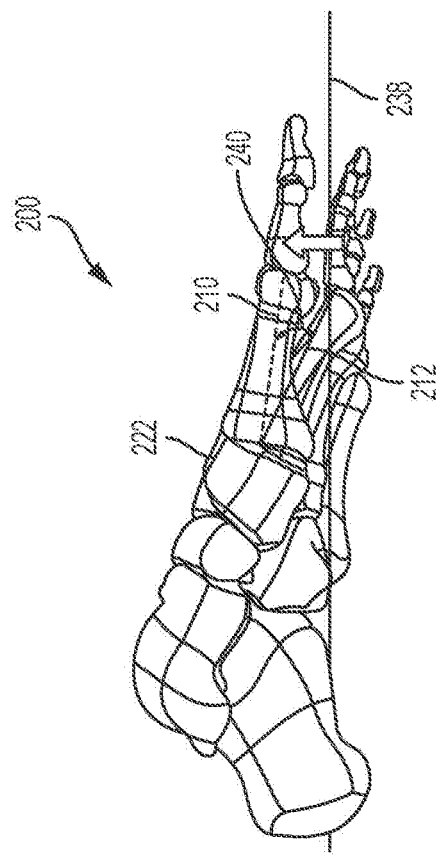
FIGS. 3A and 3B are side views of a foot showing a normal first metatarsal position and an example sagittal plane misalignment position, respectively.
Figure 3A:
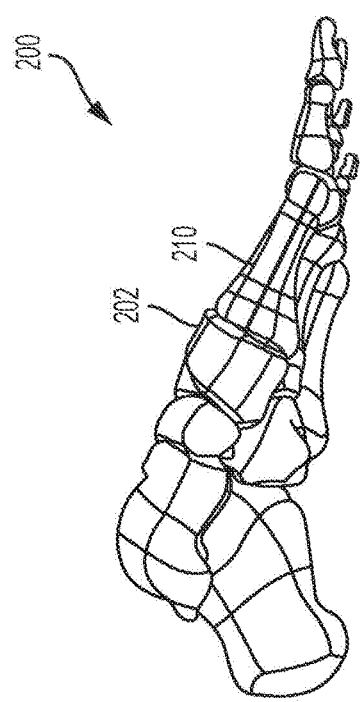

FIGS. 1-3 are different views of a foot 200 showing example anatomical misalignments that may occur and be corrected using a fulcrum according to the present disclosure. Such misalignment may be caused by a hallux valgus (bunion), natural growth deformity, or other condition causing anatomical misalignment. FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

A bi-planar instrument according to the disclosure can define a spacer body extending a medial to lateral direction (e.g., parallel to the frontal plane) of the foot that is coupled to a fulcrum body extending in a proximal to distal direction (e.g., parallel to sagittal plane) of the foot. A connecting member can couple the spacer body to the fulcrum body and transition from the frontal plane to the sagittal plane. In some examples, the connecting member can conform to (e.g., contact) a region of the metatarsal being realigned on the proximal end face of the metatarsal and also on a proximal end of a lateral side of the metatarsal. The bi-planar instrument can be used as part of a bone positioning technique to correct an anatomical misalignment of a bone or bones. In some applications, the technique involves realigning a metatarsal relative to an adjacent cuneiform and/or adjacent metatarsal. The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal or portion thereof for realignment and thereafter realigning the metatarsal in one or more planes, two or more planes, or all three planes. After suitably realigning the metatarsal, the metatarsal can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less in the transverse plane and/or sagittal plane. In certain embodiments, anatomical misalignment can be corrected in both the transverse plane and the frontal plane.

In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal.

In some applications, a bi-planar instrument is used as part of a realignment technique to anatomically align first metatarsal 210 or a portion thereof by reducing the IMA from over 10 degrees to about 10 degrees or less (e.g., to an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal is axially rotated between about 4 degrees to about 30 degrees or more. In some embodiments, a bi-planar instrument is used as part of a realignment technique to anatomically align the metatarsal by reducing the metatarsal rotation from about 4 degrees or more to less than 4 degrees (e.g., to about 0 to 2 degrees) by rotating the metatarsal with respect to the medial cuneiform.

A bi-planar instrument that defines a spacer body coupled to a fulcrum body according to the disclosure may be useful to provide a unitary structure (e.g., prior to or after being assembled) that can be positioned between two adjacent, intersecting joint spaces: a first joint space between opposed ends of a metatarsal and cuneiform and an intermetatarsal space between adjacent metatarsals. The spacer body can include a first portion insertable into the joint space and a second portion that projects above the joint space. The second portion projecting above the joint space can be coupled to a bone preparation guide, thereby facilitating positioning of the bone preparation guide over the metatarsal and/or cuneiform between which the spacer body is positioned. The fulcrum body can establish and/or maintain space between adjacent bones being moved, preventing lateral translation or base shift of the bones during rotation and/or pivoting.

For example, the bi-planar instrument can include a spacer body positionable in the joint space between first metatarsal 210 and medial cuneiform 222. The spacer body can be coupled to a bone preparation guide. The bone preparation guide may include a receiving slot into which a projecting end of the spacer body is positioned, thereby orienting the bone preparation guide relative to the joint space via the spacer body positioned therein. The bone preparation guide may include at least one cutting slot positioned over an end of first metatarsal 210 and/or an end of medial cuneiform 222 to be cut, such as at least one metatarsal side cutting slot positionable over an end of first metatarsal 210 to be cut and at least one cuneiform cutting slot positionable over an end of medial cuneiform 222 to be cut.

The bi-planar instrument can also include a fulcrum body positionable in a joint space between first metatarsal 210 and second metatarsal 212. The fulcrum body can be inserted in the notch between first metatarsal 210 and second metatarsal 212 at the base of the metatarsals (e.g., adjacent respective cuneiforms) before moving the first metatarsal, e.g., to help avoid the proximal-most base of the first metatarsal 210 from shifting toward the proximal-most base of the second 212. The fulcrum body can provide a point about which first metatarsal 210 can rotate and/or pivot while helping minimize or avoid base compression between the first metatarsal and the second metatarsal. In addition, use of the fulcrum body may cause first metatarsal 210 and medial cuneiform 222 to be better angled relative to guide slots positioned over the end faces of the bones (of the bone preparation guide engaged with the spacer body), providing a better cut angle through the guide slots than without use of the fulcrum body. This can help reduce or eliminate unwanted spring-back, or return positioning, of first metatarsal 210 after initial realignment of the metatarsal.

Figure 4A:
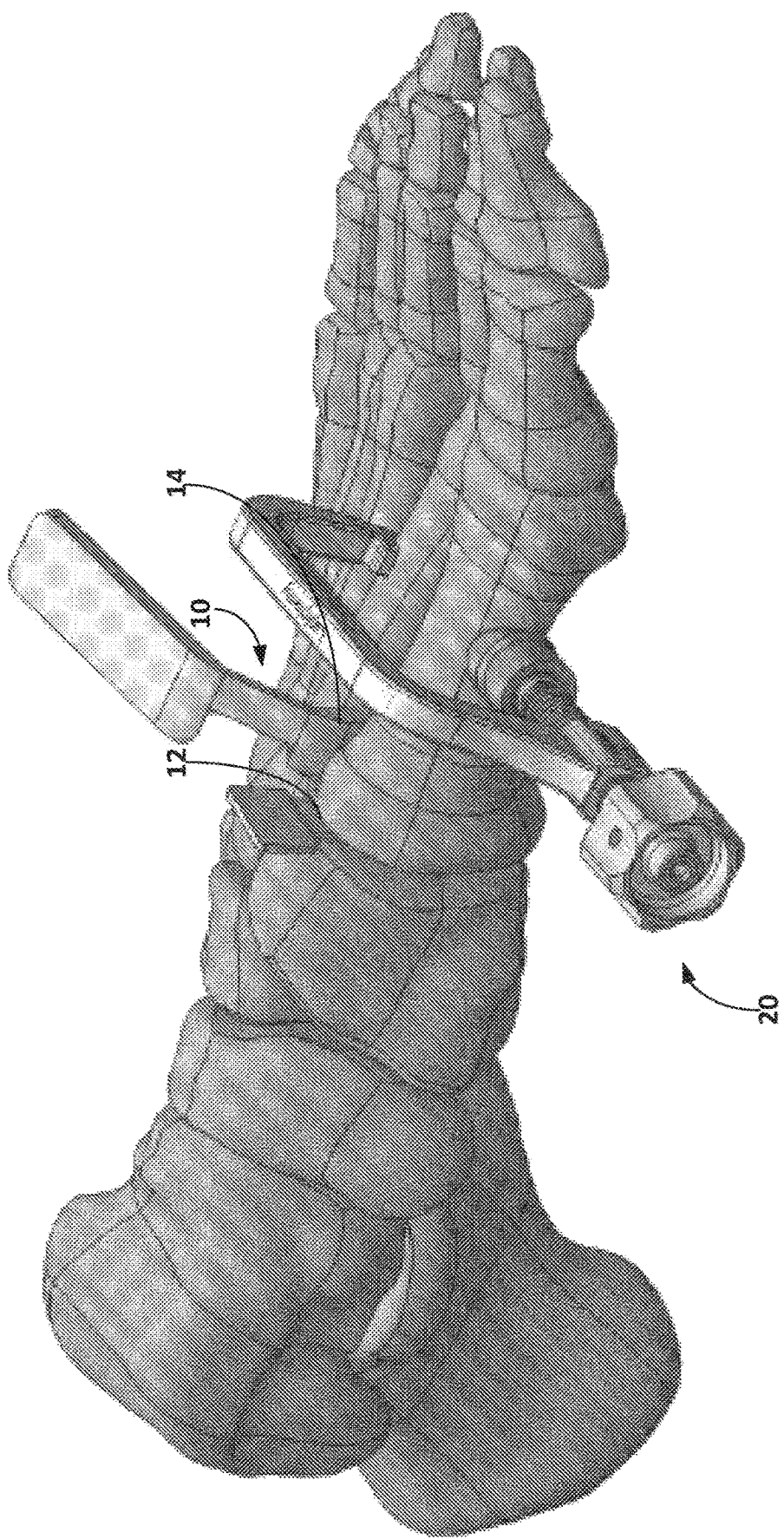
FIGS. 4A and 4B are perspective and top views, respectively, of an example bone positioning operation in which a bi-planar instrument is positioned in a first joint space and an intersecting second joint space.
Figure 4B:
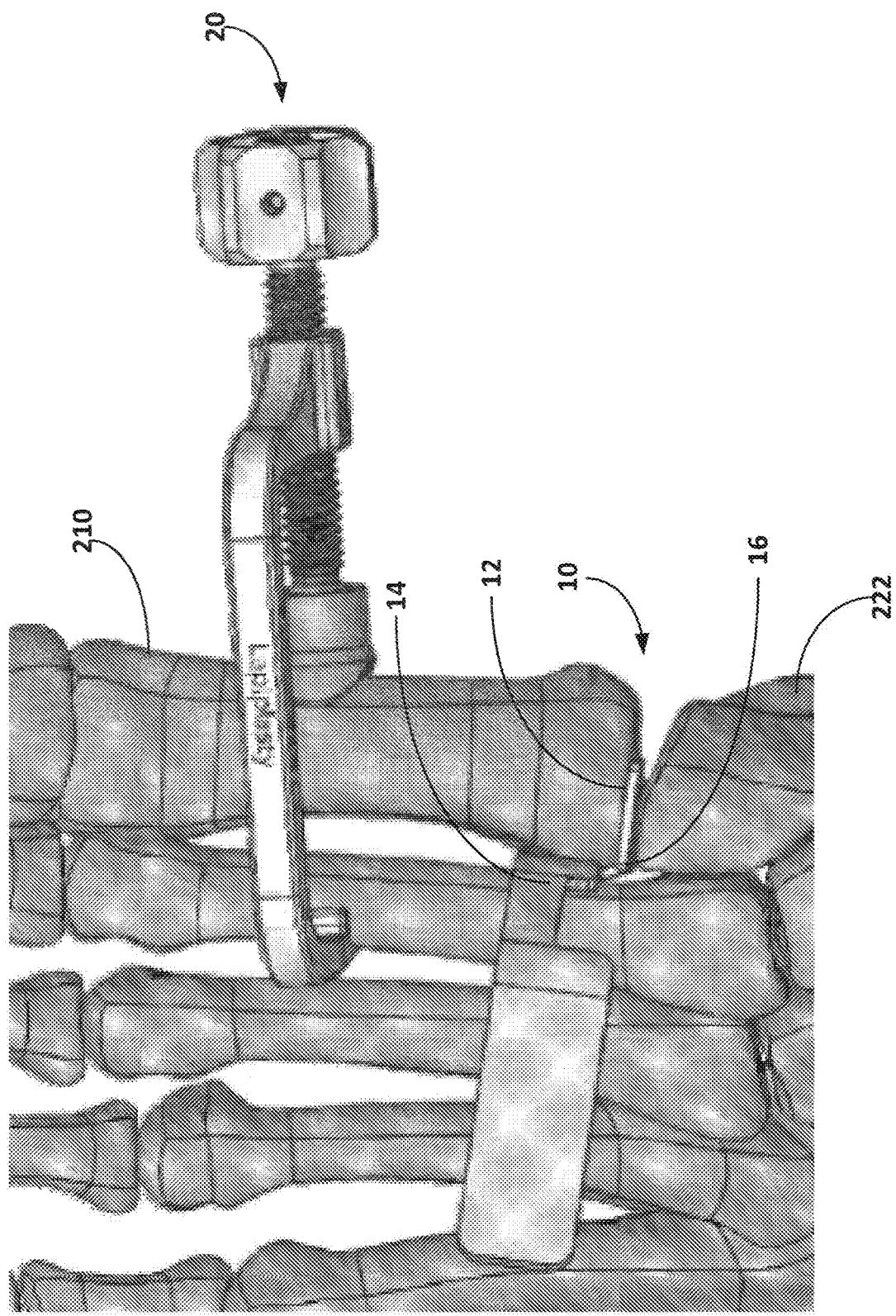

FIGS. 4A and 4B (referred to collectively as FIG. 4) are perspective and top views, respectively, of an example bone positioning operation in which a bi-planar instrument 10 is positioned in a first joint space and an intersecting second joint space, where a bone forming the first and second joint spaces is being realigned relative to one or more adjacent bones. In particular, FIG. 4 illustrates a bi-planar instrument 10 having a spacer body 12 coupled to a fulcrum body 14 via a connecting or bridge member 16. Spacer body 12 is positioned at an intersection between an end of first metatarsal 210 and opposed medial cuneiform 222. Fulcrum body 14 is positioned between first metatarsal 210 and second metatarsal 212. Bi-planar instrument 10 may optionally be used in conjunction with other surgical devices, such as a bone positioning guide 20 and a bone preparation guide 30 (FIG. 6). Additional details on example bone positioning guides, bone preparation guides, and related techniques are described in U.S. patent application Ser. No. 14/981,335, filed Dec. 28, 2015, and U.S. patent application Ser. No. 15/236,464, filed Aug. 14, 2016, the entire contents of which are incorporated herein by reference.

As shown in the example of FIG. 4, spacer body 12 can be positioned between opposed end of adjacent bones, such as opposed ends of a metatarsal (e.g., first metatarsal 210) and cuneiform (e.g., medial cuneiform 222) separated by a joint space. Spacer body 12 can define a length configured to be inserted into the joint space between the two bones (e.g., with at least a portion of the body projecting dorsally above the joint space), a thickness configured to extend between the metatarsal and the opposed cuneiform (e.g., with first metatarsal 210 and medial cuneiform 222 contacting opposed sides of the spacer body), and a width configured to extend in a medial to lateral direction across the foot.

Spacer body 12 can be positioned at any suitable location across the joint space (e.g., in the front plane). The specific positioning of spacer body 12 in use may be established by bridge member 16 coupled to fulcrum body 14. For example, when bi-planar instrument 10 is inserted into the joint space, bridge member 16 may contact a proximal-lateral corner or region of first metatarsal 210. This can limit the extent to which spacer body 12 can shift medially across the joint space, helping to fix the spacer body in the medial to lateral direction (e.g., in the frontal plane). In other examples, bi-planar instrument 10 can be inserting into the joint space without the corner defined by bridge member 16 contacting a bone (e.g., first metatarsal).

Although not illustrated in FIG. 4, in different examples, spacer body 12 can be engageable with and separable from bone preparation guide 30 or may be integral with (e.g., permanently coupled to) the bone preparation guide. The positioning of spacer body 12 in the joint space can dictate the positioning of bone preparation guide 30 coupled thereto and, correspondingly, the guiding of a bone preparation instrument facilitated by the bone preparation guide.

Bi-planar instrument 10 also includes fulcrum body 14. Fulcrum body 14 may be positioned distally of a bone positioning guide 20 between first metatarsal 210 and second metatarsal 212 or, in other applications, distally of the guide. As illustrated, fulcrum body 14 of bi-planar instrument 10 is shown proximally of bone positioning guide 20, with the fulcrum body being positioned in the joint space between the first metatarsal and second metatarsal (e.g., at the ends of the first and second metatarsals abutting the medial and intermediate cuneiform bones, respectively). In still other examples, fulcrum body 14 can be positioned in the intermetatarsal space between first metatarsal 210 and second metatarsal 212 without using bone positioning guide 20 and/or bone preparation guide 30 (FIG. 6).

In use, the clinician can insert fulcrum body 16 between first metatarsal 210 and second metatarsal 212 (or other adjacent bones, when not performing a metatarsal realignment) at any time prior to moving the first metatarsal (e.g., by actuating bone positioning guide 20 or other means of manipulating the bone). In one embodiment, the clinician prepares the joint being operated upon to release soft tissues and/or excise the plantar flare from the base of the first metatarsal 210. Either before or after installing bone positioning guide 20 over adjacent bones, the clinician inserts bi-planar instrument 10 in the joint spaces. The clinician can insert spacer body 12 in the joint space between first metatarsal 210 and medial cuneiform 222 and also insert fulcrum body 14 in the joint space between first metatarsal 210 and second metatarsal 212.

After inserting bi-planar instrument 10, the clinician can actuate bone positioning guide 20. In the case of a left foot as shown in FIG. 4, actuation of bone positioning guide 20 causes the first metatarsal 210 to rotate counterclockwise in the frontal plane (from the perspective of a patient) and also pivot in the transverse plane about the fulcrum body. In the case of a right foot (not shown), actuation causes the first metatarsal to rotate clockwise in the frontal plane (from the perspective of a patient) and also pivot in the transverse plane about the fulcrum. Thus, for both feet, actuation of bone positioning guide 20 can supinate the first metatarsal in the frontal plane and pivot the first metatarsal in the transverse plane about fulcrum body 14.

Before or after actuating bone positioning guide 20 (when used), the clinician can engage a bone preparation guide with a portion of spacer body 12 projecting from the joint space between first metatarsal 210 and medial cuneiform 222. Spacer body 12 may have a length effective to engage a bone preparation guide thereto. In some implementations, the clinician installs a separate, removable bone preparation guide 30 onto spacer body 12 after inserting bi-planar instrument 10 into the joint spaces. The clinician can attach the bone preparation guide 30 before or after attaching bone positioning guide 20. The clinician can use bone preparation guide 30 to guide a bone preparation instrument, such as a cutting blade, to prepare an end of first metatarsal 210 and an opposed end of medial cuneiform 222. The clinician can prepare one or both ends of the bones before and/or after engaging bone preparation guide 20 to move first metatarsal 210 in at least one plane, such as the transverse plane and/or frontal plane.

Figure 5B:
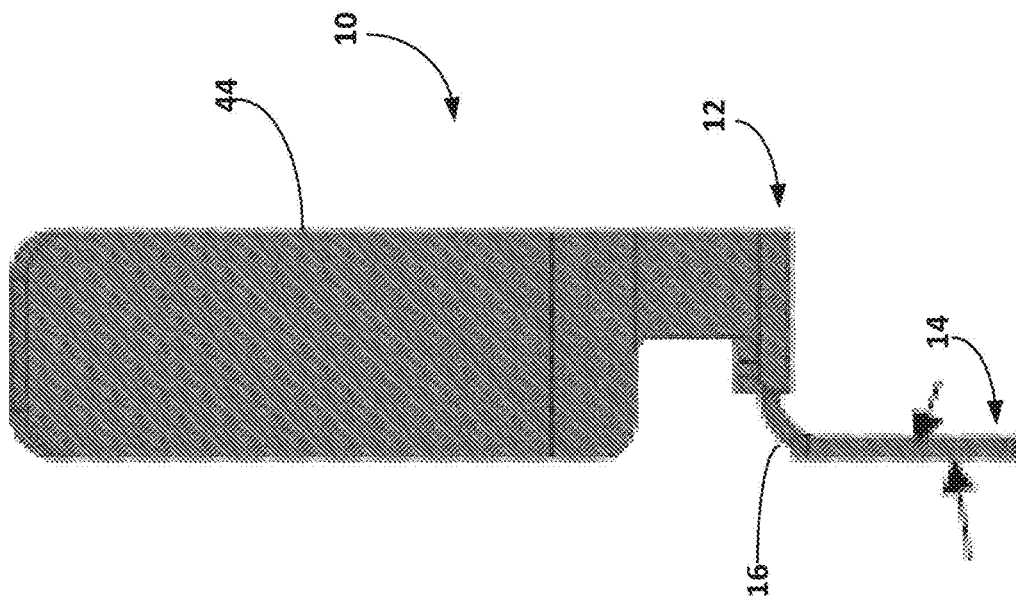
FIGS. 5A and 5B are perspective and top views, respectively, of an example configuration of the bi-planar instrument of FIGS. 4A and 4B.
Figure 5A:
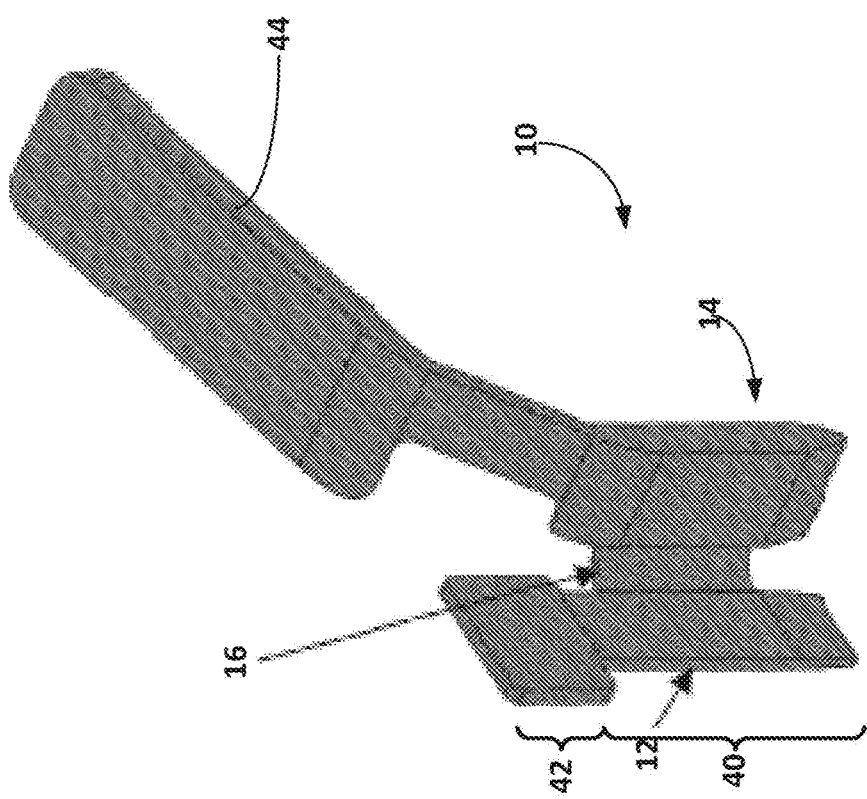

FIGS. 5A and 5B (collectively referred to as FIG. 5) are perspective and top views, respectively, of an example configuration of bi-planar instrument 10. As shown in this example, instrument 10 includes spacer body 12 coupled to fulcrum body 14. In some examples, spacer body 12 and fulcrum body 14 are intersecting body members coupled together without an intervening coupling member. In other examples, such as the example illustrated in FIG. 5, an intermediate coupling member 16 joins spacer body 12 to fulcrum body 14.

Coupling member 16 may be in the form of a bridge extending between spacer body 12 and fulcrum body 14. In use, spacer body 12 may be configured to extend in a frontal plane of the foot, between first metatarsal 210 and medial cuneiform 222. Fulcrum body 14 may be configured to extend in a sagittal plane of the foot, between first metatarsal 210 and second metatarsal 212. Bridge member 16 can define a bended and/or angled region of bi-planar instrument 10 that transitions from the frontal plane to the sagittal plane. For example, bridge member may be configured to extend from a proximal side of first metatarsal 210 to a lateral side of the metatarsal. By coupling spacer body 12 to fulcrum body 14 via bridge member 16, the position and orientation of the two bodies relative to each other and/or relative to first metatarsal 210 may be fixed. This can help ensure the proper positioning of the respective bodies in use.

In general, spacer body 12 may define a length configured to be inserted into the joint space, a thickness configured to extend between the bone defining the joint space (e.g., metatarsal and the opposed cuneiform), and a width configured to extend in a medial to lateral direction partially or fully across the joint space. Spacer body 12 may define a first portion 40 configured to extend at least partially into the joint space between the metatarsal and the opposed cuneiform and a second portion 42 configured to extend above the joint space. Second portion 42 can be configured to engage a receiving cavity of a bone preparation guide or can be integrally attached to the bone preparation guide.

Fulcrum body 14 can define a length configured to be inserted into the intermetatarsal space, a thickness configured to extend between first metatarsal 210 and second metatarsal 212, and a width configured to extend in the proximal to distal direction across the foot. The thickness of fulcrum body 14 may be tapered toward the leading end to facilitate insertion of fulcrum body 14 into a space between adjacent metatarsals.

In some examples, instrument 10 includes a handle 44. Handle 44 is illustrated as being operatively connected to fulcrum body 14 although can be connected to and extend from spacer body 12 in addition to or in lieu of fulcrum body 14. Handle 44 may be any structure projecting proximally from bi-planar instrument 10 (e.g., from fulcrum body 14) that can provide a gripping location for the instrument during use. In some examples, such as the example illustrated in FIG. 5, handle 44 can project angularly away from fulcrum body 14 to define a tissue retraction space. The tissue retraction space may be a region bounded on one side by fulcrum body 14 and one side of handle 44. In use, body fulcrum 14 may be inserted into an intermetatarsal space with handle 44 extending out of the surgical incision and over an epidermal layer with tissue captured in the tissue retraction space. For example, fulcrum body 14 may be inserted into an intermetatarsal space with handle 44 projecting toward the lateral side of the foot being operated upon. The tissue retraction space may help retract tissue and push the tissue laterally away from a first metatarsal and/or medial cuneiform being operated upon.

To form a tissue retraction space, handle 44 may project away from fulcrum body 14, e.g., linearly at a zero-degree angle and/or laterally at a non-zero-degree angle. The specific angular orientation of the handle 44 relative to the body 14 may vary. However, in some examples, handle 44 is oriented relative to the fulcrum body 14 so a handle axis intersects an axis extending along the length of the fulcrum body at an acute angle ranging from 5 degrees to 85 degrees, such as from 20 degrees to 75 degrees, or from 35 degrees to 55 degrees.

In general, bi-planar instrument 10 can be fabricated from any suitable materials. In different examples, the instrument may be fabricated from metal, a polymeric material, or a hybrid form of multiple metals and/or polymeric materials. In addition, although spacer body 12 and fulcrum body 14 are generally illustrated as having rectangular cross-sectional shapes, one or both bodies can define a different generally polygonal cross-sectional shape (e.g., square, hexagonal) and/or generally arcuate cross-sectional shape (e.g., circular, elliptical).

Figure 5D:
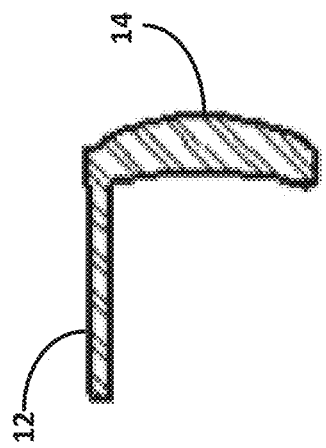
FIGS. 5C and 5D are perspective and sectional views, respectively, showing an example configuration of a fulcrum body defining a concave bone contacting surface.
Figure 5C:
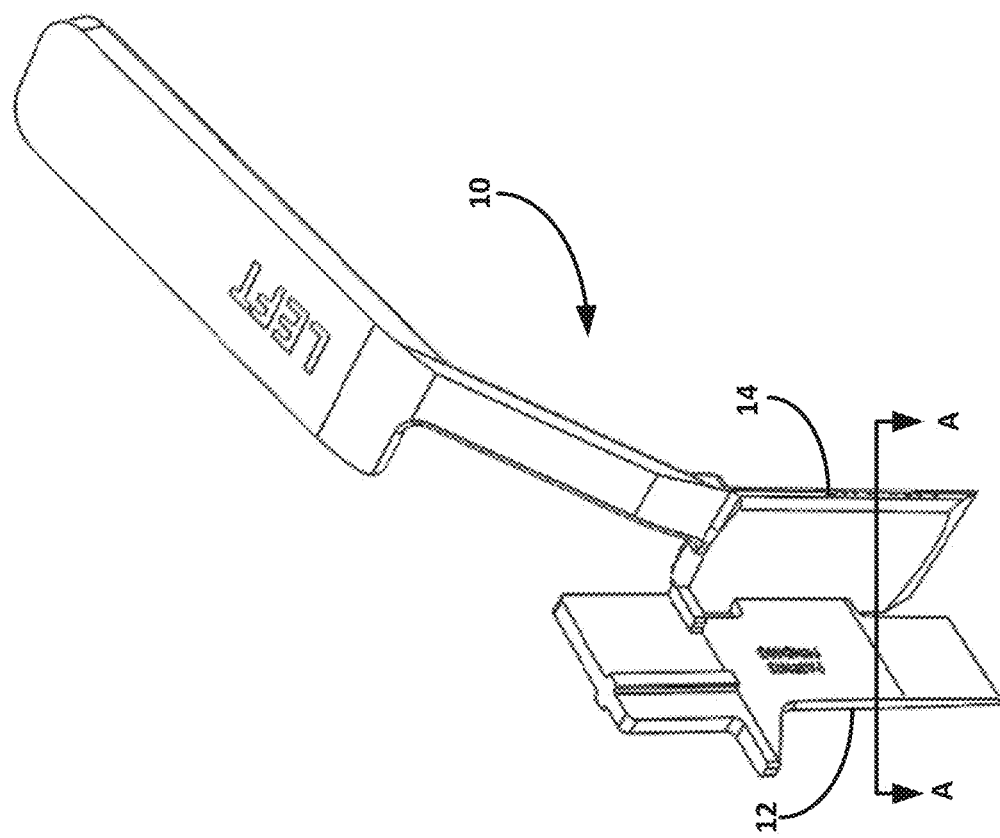

For example, while spacer body 12 and/or fulcrum body 14 may define a planar face contacting a bone, one or both bodies may alternatively have non-planar faces contacting the bone. FIGS. 5C and 5D are perspective and sectional views, respectively, showing an example configuration of fulcrum body 14 defining a concave bone contacting surface. FIGS. 5E and 5F are perspective and sectional views, respectively, showing an example configuration of fulcrum body 14 defining a convex bone contacting surface.

As still another example, fulcrum body 14 of bi-planar instrument 10 may be angled in the sagittal plane, e.g., such that the plantar end of the fulcrum body extends farther medially than the dorsal end of the fulcrum body or, alternatively, the plantar end of the fulcrum body extend farther laterally than the dorsal end of the fulcrum body. Angling fulcrum body 14 in the sagittal plane may be useful to help dorsiflex or plantarflex the metatarsal being moved, e.g., by providing an angled fulcrum surface tending to redirect the metatarsal in the sagittal plane. The foregoing discussion of example fulcrum body shape and/or profile configurations can be employed in a standalone fulcrum device in the techniques described herein (e.g., without using an attached spacer body).

In some examples, bi-planar instrument 10 (e.g., spacer body 12, fulcrum body 14, bridge member 16) will be formed as a unitary structure, e.g., by milling, casting, or molding the components to be permanently and structurally integrated together. In other examples, one or more the features may be fabricated as separate components that are subsequently joined together.

In some examples, bi-planar instrument 10 is used as part of a metatarsal realignment procedure in which a metatarsal is realigned relative to an adjacent cuneiform and/or metatarsal in one or more planes, such as two or three planes. Additional details on example bone realignment techniques and devices with which instrument 10 may be used are described in U.S. Pat. No. 9,622,805, titled "BONE POSITIONING AND PREPARING GUIDE SYSTEMS AND METHODS," filed on Dec. 28, 2015 and issued Apr. 18, 2017, and U.S. Pat. No. 9,936,994, titled "BONE POSITIONING GUIDE," filed on Jul. 14, 2016 and issued on Apr. 10, 2018, and US Patent Publication No. 2017/0042599 titled "TARSAL-METATARSAL JOINT PROCEDURE UTILIZING FULCRUM," filed on Aug. 14, 2016. The entire contents of each of these documents are hereby incorporated by reference.

Figure 6A:
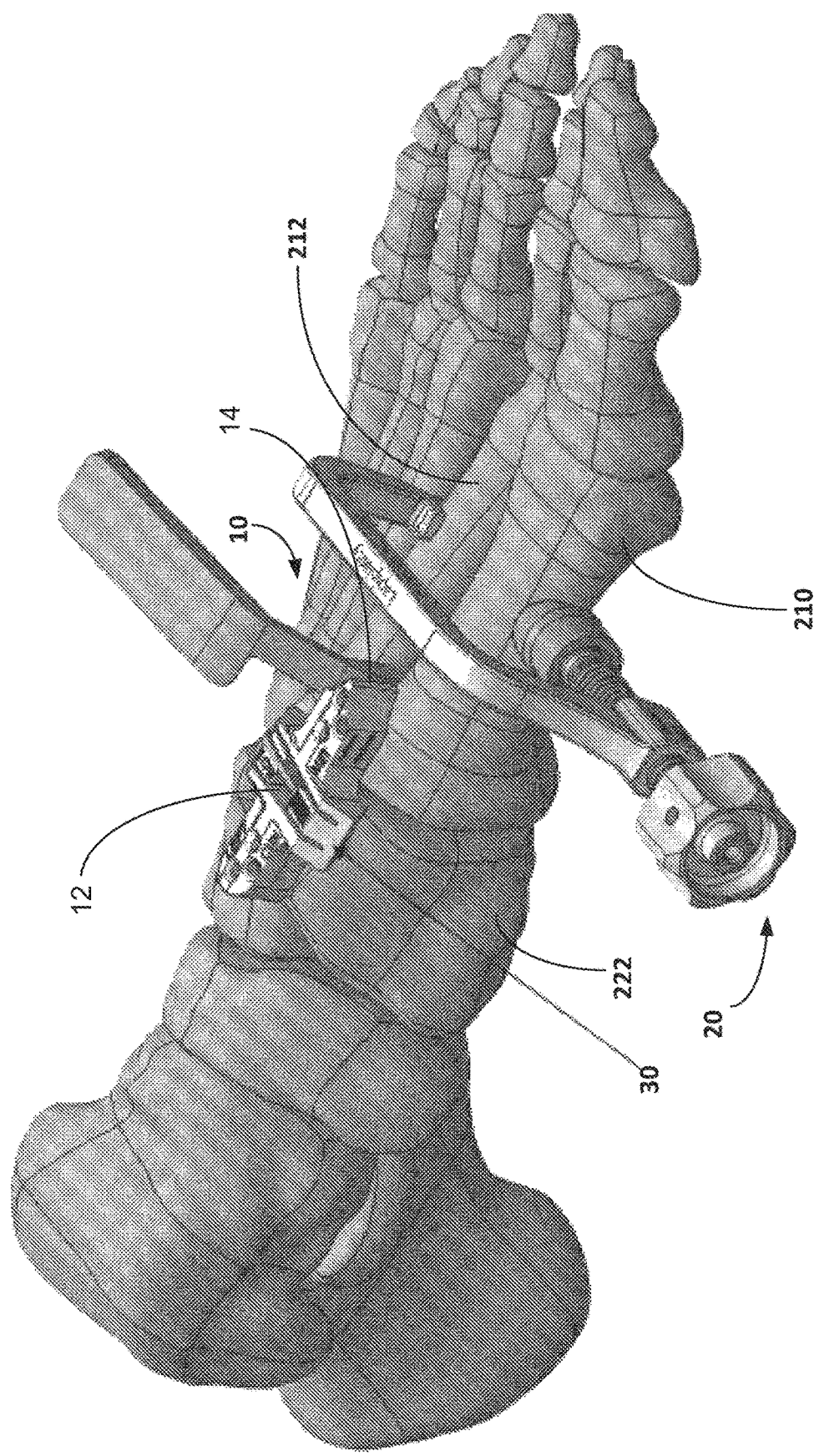
FIGS. 6A and 6B are perspective and top views, respectively showing an example bone preparation guide that may be used as part of a surgical procedure involving a bi-planar instrument.
Figure 6B:
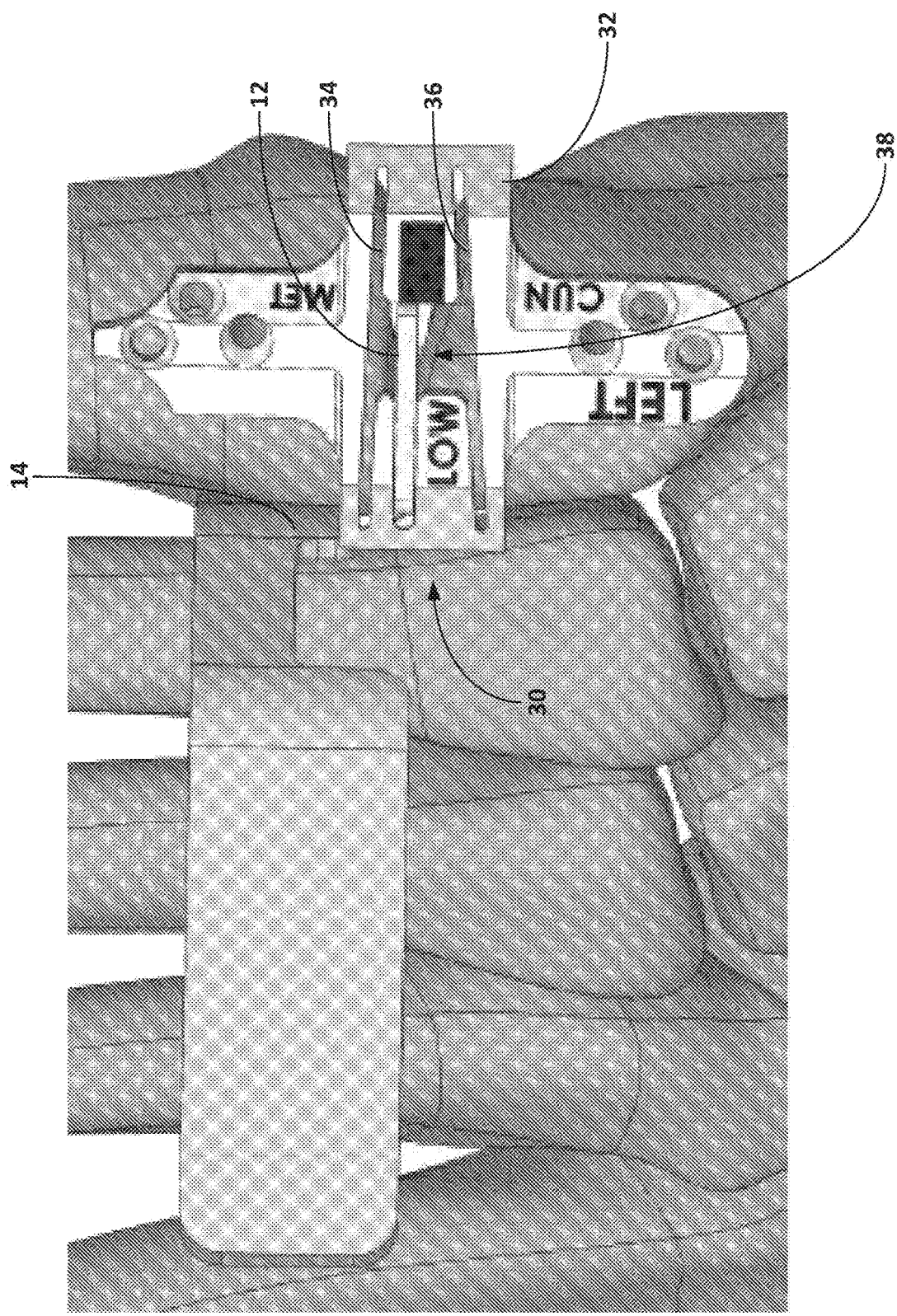

FIGS. 6A and 6B (collectively referred to as FIG. 6) are perspective and top views, respectively showing an example bone preparation guide 30 that may be used as part of a surgical procedure involving bi-planar instrument 10. In some examples, bone preparation guide 30 includes a body 32 defining a first guide surface 34 to define a first preparing plane and a second guide surface 36 to define a second preparing plane. A tissue removing instrument (e.g., a saw, rotary bur, osteotome, etc., not shown) can be aligned with the surfaces to remove tissue (e.g., remove cartilage or bone and/or make cuts to bone). The first and second guide surfaces 34, 36 can be spaced from each other by a distance, (e.g., between about 2 millimeters and about 10 millimeters, such as between about 4 and about 7 millimeters). In different configurations, the first and second guide surfaces can be parallel to each other or angled relative to each other, such that cuts to adjacent bones using the guide surfaces will be generally parallel or angled relative to each other.

In some configurations, the first and second guide surfaces 34, 36 are bounded by opposed surfaces to define guide slots. Each slot can be sized to receive a tissue removing instrument to prepare the bone ends. In either case, an opening 38 may be defined in body 32 of bone preparation guide 30 for receiving spacer body 12. In use, a clinician can insert bi-planar instrument 10 into the joint space between first metatarsal 210 and medial cuneiform 222 as well as between first metatarsal 210 and second metatarsal 212. The clinician can then insert bone preparation guide 30 on spacer body 12 of the instrument, e.g., by aligning opening 38 with the portion of spacer body 12 projecting dorsally from the joint space. Alternatively, as noted above, bone preparation guide 30 and bi-instrument 10 may be preassembled (e.g., removably coupled together or permanently and fixedly joined together) such that inserting bi-planar instrument 10 into the joint space between adjacent bones simultaneously positions bone preparation guide 30 over one or more bones to be prepared.

In the illustrated example, bone preparation guide 30 extends from a first end positioned over first metatarsal 210 and a second end positioned over medial cuneiform 222. One or both ends of the body can define one or more fixation apertures configured to receive fixation pin(s) for securing bone preparation guide 30 to one or more bones.

Bone preparation facilitated by bone preparation guide 30 can be useful, for instance, to facilitate contact between leading edges of adjacent bones, separated by a joint, or different portions of a single bone, separated by a fracture, such as in a bone alignment and/or fusion procedure. A bone may be prepared using one or more bone preparation techniques. In some applications, a bone is prepared by cutting the bone. The bone may be cut transversely to establish a new bone end facing an opposing bone portion. Additionally or alternatively, the bone may be prepared by morselizing an end of the bone. The bone end can be morselized using any suitable tool, such as a rotary bur, osteotome, or drill. The bone end may be morselized by masticating, fenestrating, crushing, pulping, and/or breaking the bone end into smaller bits to facilitate deformable contact with an opposing bone portion.

During a surgical technique utilizing bi-planar instrument 10, a bone may be moved from an anatomically misaligned position to an anatomically aligned position with respect to another bone. Further, both the end of the moved bone and the facing end of an adjacent end may be prepared for fixation. In some applications, the end of at least one of the moved bone and/or the other bone is prepared after moving the bone into the aligned position. In other applications, the end of at least one of the moved bone and/or the other bone is prepared before moving the bone into the aligned position. In still other applications, the end of one of the moved bone and the other bone is prepared before moving the bone into the aligned position while the end of the opposite facing bone (either the moved bone or the other bone) is prepared after moving the bone into the aligned position.

Movement of one bone relative to another bone can be accomplished using one or more instruments and/or techniques. In some examples, bone movement is accomplished using a bone positioning device, e.g., that applies a force through one or more moving components to one bone, causing the bone to translate and/or rotate in response to the force. This may be accomplished, for example, using a bone positioning guide that includes a bone engagement member, a tip, a mechanism to urge the bone engagement member and the tip towards each other, and an actuator to actuate the mechanism. Additionally or alternatively, bone movement may be accomplished using a compressor-distractor by imparting movement to one bone relative to another bone as the compressor-distractor is positioned on substantially parallel pins, causing the pins to move out of their substantially parallel alignment and resulting in movement of the underlying bones in one plane (e.g., frontal plane, sagittal plane, transverse plane), two or more planes, or all three planes. As yet a further addition or alternative, a clinician may facilitate movement by physically grasping a bone, either through direct contact with the bone or indirectly (e.g., by inserting a K-wire, grasping with a tenaculum, or the like), and moving his hand to move the bone.

When used, the clinician can insert bi-planar instrument 10 between first metatarsal 210 and second metatarsal 212 and between first metatarsal 210 and medial cuneiform 222 (or other adjacent bones, when not performing a first metatarsal realignment) at any time prior to moving the first metatarsal (e.g., by actuating a bone positioning guide or otherwise manipulating the bone). In one embodiment, the clinician prepares the joint being operated upon to release soft tissues and/or excise the plantar flare from the base of the first metatarsal 210. Either before or after installing an optional bone positioning guide over adjacent bones, the clinician inserts the instrument 10 at the joint between the first metatarsal and the second metatarsal and at the joint between the first metatarsal and medial cuneiform. The clinician can subsequently actuate bone positioning guide 20 (e.g., when used). As distal portion of first metatarsal can move toward the second metatarsal in the transverse plane to close the IMA, thereby pivoting a proximal portion of the first metatarsal about fulcrum body 14 and reducing the IMA between the first metatarsal and the second metatarsal. The use of fulcrum body 14 can minimize or eliminate base compression between adjacent bones being operated upon.

The clinician can additionally engage bone preparation guide 30 with spacer body 12 and use the bone preparation guide to prepare an end of first metatarsal 210 and an end of medial cuneiform 222. The clinician may prepare the ends of one or both bones before or after moving the first metatarsal in one or more planes (e.g., using bone preparation guide 30). In either case, the clinician may optionally provisionally fixate the moved position (e.g., by inserting a k-wire or other fixation element) into first metatarsal 210 and an adjacent bone (e.g., second metatarsal 212, medial cuneiform 222). The clinician can remove bone positioning guide 20 and bi-planar instrument 10 from the foot, e.g., before or after optionally provisionally fixating. In either case, the clinician may permanently fixate the prepare bone ends, causing the prepared bone ends to fuse together.

In one example technique, after customary surgical preparation and access, a bone preparation instrument can be inserted into the joint (e.g., first tarsal-metatarsal joint) to release soft tissues and/or excise the plantar flare from the base of the first metatarsal 210. Excising the plantar flare may involve cutting plantar flare off the first metatarsal 210 so the face of the first metatarsal is generally planar. This step helps to mobilize the joint to facilitate a deformity correction. In some embodiments, the dorsal-lateral flare of the first metatarsal may also be excised to create space for the deformity correction (e.g., with respect to rotation of the first metatarsal). In certain embodiments, a portion of the metatarsal base facing the medial cuneiform can be removed during this mobilizing step.

An incision can be made and, if a bone positioning instrument is going to be used, one end (e.g., a tip) of a bone positioning guide 20 inserted on the lateral side of a metatarsal other than the first metatarsal 210, such as the second metatarsal 212. The tip can be positioned proximally at a base of the second metatarsal 212 and a third metatarsal 294 interface.

Before or after attaching the optional bone positioning guide 20, the clinician can insert bi-planar instrument 10 into the joint. The clinician can position spacer body 12 into the joint space between first metatarsal 210 and medial cuneiform 222 while simultaneously positioning fulcrum body 14 in the joint space between first metatarsal 210 and second metatarsal 212.

When bi-planar instrument 10 includes bridge member 16, the bridge member can be positioned in contact with a proximal-lateral corner of first metatarsal 210, helping to appropriately position spacer body 12 and fulcrum body 14 relative to each other. For example, bridge member 16 may position spacer body 12 substantially centered or on a lateral half of the joint space between first metatarsal 210 and medial cuneiform 222. Bridge member 16 may further position fulcrum body 14 in the notch between first metatarsal 210 and second metatarsal 212 at the base of the metatarsals (e.g., adjacent respective cuneiform). Fulcrum body 14 can provide a point about which first metatarsal 210 can rotate and/or pivot while helping minimize or avoid base compression between the first metatarsal and the second metatarsal.

In applications utilizing bone positioning guide 20, one or more movable features of the bone positioning guide can be moved to reduce the angle (transverse plane angle between the first metatarsal and the second metatarsal) and rotate the first metatarsal about its axis (frontal plane axial rotation). The first metatarsal 210 can be properly positioned with respect to the medial cuneiform 222 by moving a bone engagement member of bone positioning guide 20 with respect to a tip of the bone positioning guide. In some embodiments, such movement simultaneously pivots the first metatarsal with respect to the cuneiform and rotates the first metatarsal about its longitudinal axis into an anatomically correct position to correct a transverse plane deformity and a frontal plane deformity. Other instrumented and/or non-instrumented approaches can be used to adjust a position of first metatarsal 210 relative to medial cuneiform 222. Thus, other applications utilizing bi-planar instrument 10 may be performed without utilizing bone positioning guide 20 and/or using a bone positioning guide having a different design than the specific example illustrated herein.

Independent of whether bone positioning guide 20 is used, an example technique may include positioning bone preparation guide 30 over spacer body 12 as shown in FIG. 6 (in instances in which the bone preparation guide is not integral with the spacer body). A portion of spacer body 12 projecting dorsally from the joint space between first metatarsal 210 and medial cuneiform 222 can be received in opening 38 of bone preparation guide 30. One or more fixation pins can be inserted into apertures of the bone preparation guide 30 to secure the guide to the first metatarsal 210 and the medial cuneiform 222. When bone preparation guide 30 is preassembled with bi-planar instrument 10 (e.g., removable coupled thereto or fixedly and permanently coupled thereto), insertion of bi-planar instrument 10 into the joint spaces can simultaneously position one or more guide surfaces of bone preparation guide 30 over one or more bone surfaces to be prepared (e.g., cut) using the guide surface(s).

In some applications, the end of the first metatarsal 210 facing the medial cuneiform 222 can be prepared with a tissue removing instrument guided by a guide surface of bone preparation guide 30 (e.g., inserted through a slot defined by a first guide surface and a first facing surface). In some embodiments, the first metatarsal 210 end preparation is done after at least partially aligning the bones, e.g., by actuating bone positioning guide 20 or otherwise moving the first metatarsal but after preparing the end of first metatarsal 210. In other embodiments, the first metatarsal 210 end preparation is done before the alignment of the bones.

In addition to preparing the end of first metatarsal 210, the end of the medial cuneiform 222 facing the first metatarsal 210 can be prepared with the tissue removing instrument guided by a guide surface of bone preparation guide 30 (e.g., inserted through a slot defined by a second guide surface and a second facing surface). In some embodiments, the medial cuneiform 222 end preparation is done after the alignment of the bones. In yet other embodiments, the medial cuneiform 222 end preparation is done before the alignment of the bones. In embodiments that include cutting bone or cartilage, the cuneiform cut and the metatarsal cut can be parallel, conforming cuts, or the cuts can be angled relative to each other. In some examples, a saw blade can be inserted through a first slot to cut a portion of the medial cuneiform and the saw blade can be inserted through a second slot to cut a portion of the first metatarsal.

When bone preparation guide 30 is separable from bi-planar instrument 10, any angled/converging pins can be removed and the bone preparation guide 30 can be lifted off substantially parallel first and second pins also inserted into the bones (or all fixation pins can be removed). Bi-planar instrument 10 (or at least spacer body 12 of the instrument) can removed from the foot. In some examples, a compressor-distractor is positioned down over the parallel pins remaining in the bones or otherwise attached to the bones.

In applications where bone positioning guide 20 is utilized, the bone positioning guide may be removed before or after bone preparation guide 30 is removed and, when used, a compressor-distractor is installed. In either case, in some examples, a temporary fixation device such as an olive pin, k-wire, or other fixation structure may be used to maintain the position of the underlying bones (e.g., first metatarsal 210 relative to medial cuneiform 222), e.g., while bone preparation guide 30 is removed and, optionally, a compressor-distractor is installed and/or during permanent fixation.

When a compressor-distractor is pinned to underlying bones (e.g., first metatarsal 210 and medial cuneiform 222), the compressor-distractor may be actuated to distract the underlying bones. With the underlying bones distracted, the clinician may clean or otherwise prepare the space between the bones and/or the end face of one or both bones. The clinician may clean the space by removing excess cartilage, bone, and/or other cellular debris that may natively exist or may have been created during the bone preparation step that may inhibit infusion.

Independent of whether the clinician utilizes compressor-distractor 100 to distract the underlying bones for cleaning, the clinician can engage the compressor-distractor to compress the first metatarsal toward the medial cuneiform.

With the end faces pressed together (optionally via actuation of a compressor-distractor), the clinician may provisionally and/or permanently fixate the bones or bones portions together. For example, one or more bone fixation devices can be applied across the joint and to the two bones to stabilize the joint for fusion, such as two bone plates positioned in different planes. For example, a first bone plate may be positioned on a dorsal-medial side of the first metatarsal and medial cuneiform and a second bone plate positioned on a medial-plantar side of the first metatarsal and the medial cuneiform. In some embodiments, a bone plate used for fixation can be a helical bone plate positioned from a medial side of the cuneiform to a plantar side of the first metatarsal across the joint space. The plates can be applied with the insertion of bone screws. Example bone plates that can be used as first bone plate 310 and/or second bone plate 320 are described in US Patent Publication No. US2016/0192970, titled "Bone Plating System and Method" and filed Jan. 7, 2016, which is incorporated herein by reference. Other types in configurations of bone fixation devices can be used, and the disclosure is not limited in this respect. For example, an intramedullary pin or nail may be used in addition to or in lieu of a bone plate.

Spacer body 12 and fulcrum body 14 of bi-planar instrument 10 may be permanently coupled together (e.g., such that the spacer bodies cannot be separated from each other without permanently destroying or modifying the device). Alternatively, spacer body 12 may be detachably connected to fulcrum body 14. Such a configuration may allow spacer body 12 to be removed from the joint space while leaving fulcrum body 14 in the joint space (or performing other separate actions) or vice versa.

In one implementation, for example, a clinician may insert bi-planar instrument 10 into the joint spaces and then realign one bone relative to another bone. As the bones are realigned relative to each other, fulcrum body 14 may provide a surface along which adjacent bones can slide and/or prevent compression or base shift between adjacent bones during realignment. After realigning the bones relative to each other, the clinician may detach spacer body 12 from fulcrum body 14, leaving spacer body 12 in the joint space. Bone preparation guide 30 can then be installed over spacer body 12 to facilitate preparation of one or both bones.

As another example, the clinician can insert bi-planar instrument 10 into the joint spaces and then insert bone preparation guide 30 over spacer body 12 of the bi-planar instrument 10 (in instances in which the bone preparation guide and instrument are installed separately). The clinician can then use bone preparation guide 30 to prepare the end faces of one or both bones prior to subsequent realignment. With the end faces of one or both bones suitably prepared, the clinician can remove bone preparation guide 30 and detach spacer body 12 from fulcrum body 14. Spacer body 12 can then be removed from the joint space, leaving fulcrum body 14 between adjacent bones for subsequent bone realignment.

Figure 7B:
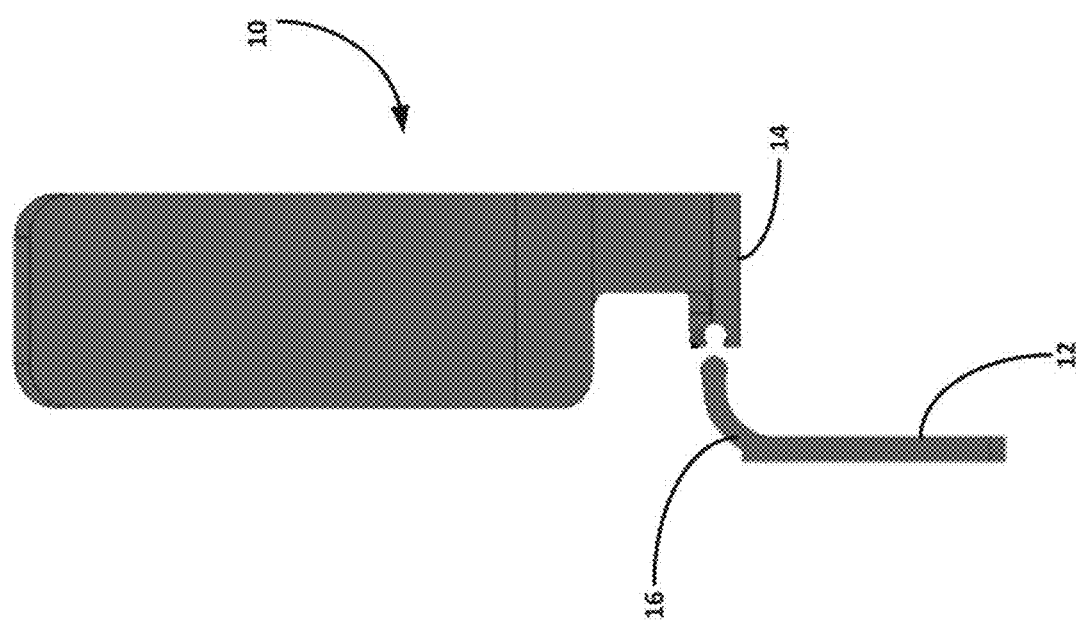
FIGS. 7A and 7B are perspective and top views, respectively, of an example configuration of a bi-planar instrument in which a spacer body is detachable from and attachable to a fulcrum body.
Figure 7A:
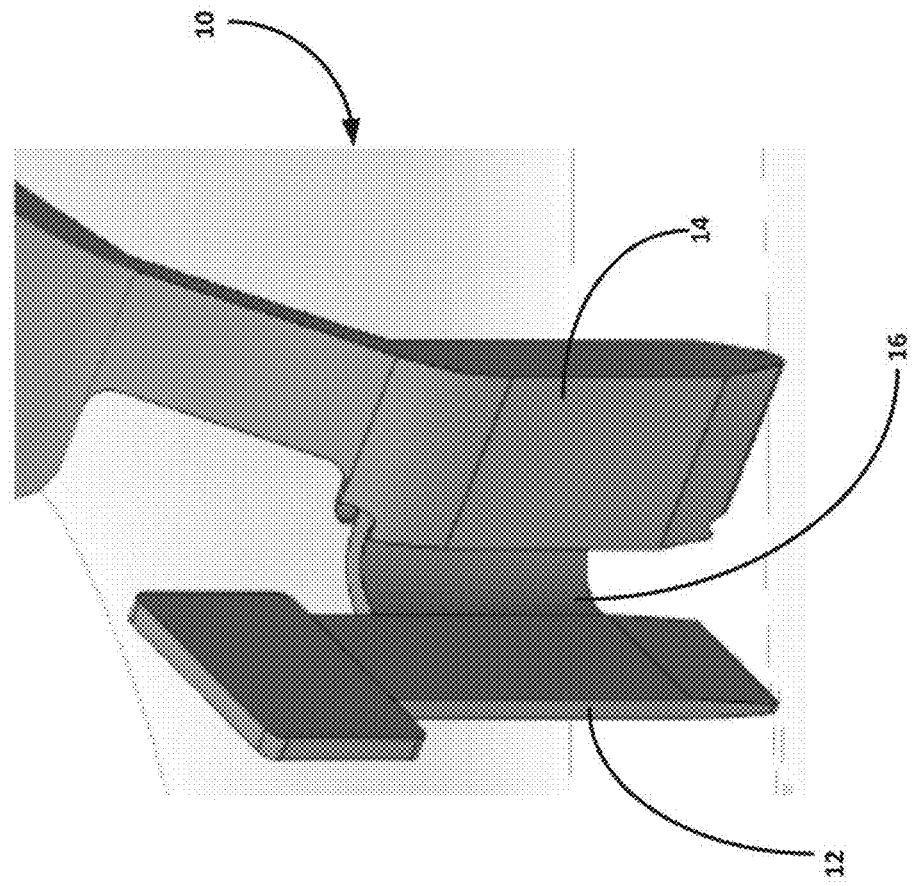

FIGS. 7A and 7B are perspective and top views, respectively, of an example configuration of bi-planar instrument 10 in which spacer body 12 is detachable from and attachable to fulcrum body 14. In this example, bridge member 16 is permanently affixed to spacer body 12 and defines an insertion end insertable into a corresponding receiving portion of fulcrum body 14. Spacer body 12 and bridge member 16 can be detached from fulcrum body 14 by sliding the spacer body and bridge member longitudinally (e.g., in a dorsal direction when inserted into the foot), allowing the spacer body and bridge member to be detached from the fulcrum body.

In other configurations, bridge member 16 may be attachable to and detachable from spacer body 12 in addition to or in lieu of being attachable to and detachable from fulcrum body 14. In still other configurations, bi-planar instrument 10 may not include a bridge member but instead may be configured with spacer body 12 connected directly to fulcrum body 14. In these configurations, spacer body 12 and fulcrum body 14 can have corresponding connections that allow the two bodies to be attachable to and detachable from each other. In general, any features described as being removably coupled to (e.g., attachable to and detachable from) each other can have complementary connection features (e.g., corresponding male and female connection features; corresponding magnetic features) that allow the features to be selectively joined together and separated from each other.

Independent of whether spacer body 12 and fulcrum body 14 are detachable from each other, bi-planar instrument 10 can join and position the two different bodies relative to each other. The relative angle between spacer body 12 and fulcrum body 14 can vary depending on the desired application (e.g., the anatomical location where bi-planar instrument 10 is intended to be inserted and/or the anatomy of the specific patient on which bi-planar instrument 10 is used). In some examples, bi-planar instrument 10 defines an interior angle between spacer body 12 and fulcrum body 14 (with or without bridge member 16) ranging from 60 degrees to 120 degrees, such as from 80 degrees to 100 degrees, or approximately 90 degrees. The angle between spacer body 12 and fulcrum body 14 may be fixed (such that the angle is not intended to be adjustable or manipulable by a clinician during use) or may be variable (such that the angle can be adjusted by a clinician within a surgical suite prior to insertion and/or while inserted into a patient undergoing a procedure in which the instrument is used).

In some examples, the angle between spacer body 12 and fulcrum body 14 is defined by a sharp transition, e.g., where the spacer body intersects the fulcrum body at the angle defined therebetween. In other examples, bi-planar instrument 10 defines a radius of curvature transitioning between spacer body 12 and fulcrum body 14, with the angle of intersection defined between the faces of the two bodies. For instance, in the illustrated examples of FIGS. 5B and 7B, bi-planar instrument 10 is illustrated as having a radius of curvature between spacer body 12 and fulcrum body 14. Configuring bi-planar instrument 10 with a curved transition between spacer body 12 and fulcrum body 14 (at least on a backside of the instrument) may be useful to provide a smooth surface to help insert the instrument into the patient, e.g., by minimizing sharp edges that can catch on the patient's tissue during insertion.

When bi-planar instrument 10 is configured with a fixed angle between spacer body 12 and fulcrum body 14, the instrument may be fabricated of a material and have a material thickness effective to substantially inhibit the clinician changing the angle between the two bodies during use of the instrument. Likewise, the instructions for use accompanying bi-planar instrument 10 may indicate that the instrument is intended to be used without manipulating the angle between spacer body 12 and fulcrum body 14.

In other configurations, the angle between spacer body 12 and fulcrum body 14 may be adjustable by the clinician. For example, the instructions for use accompanying bi-planar instrument 10 may indicate that the clinician is able to adjust the position of spacer body 12 and fulcrum body 14 relative to each other before and/or after inserting the instrument in the patient. In one example, bi-planar instrument 10 may be fabricated of a material and have a material thickness effective to allow the clinician to change the angle between spacer body 12 and fulcrum body 14 during use. For example, bi-planar instrument 10 (e.g., bridge member 16 of the instrument) may be fabricated of a malleable metal and/or polymeric material that the clinician can manipulate under hand pressure (e.g., with or without the aid of an instrument, such as a bending tool) to change the angle between spacer body 12 and fulcrum body 14.

Additionally or alternatively, bi-planar instrument 10 may include one or more flexible joints (e.g., rotating joints), which allow the angular position of spacer body 12 to be adjusted relative to fulcrum body 14. As one example, spacer body 12 may be operatively connected to fulcrum body 14 via one or more cables, allowing the angular orientation of spacer body 12 and fulcrum body 14 to change by bending the one or more cables. As another example, spacer body 12 may be operatively connected to fulcrum body 14 via a hinged connection, allowing the spacer body and fulcrum body to rotate relative to each other about the hinge.

Figure 8B:
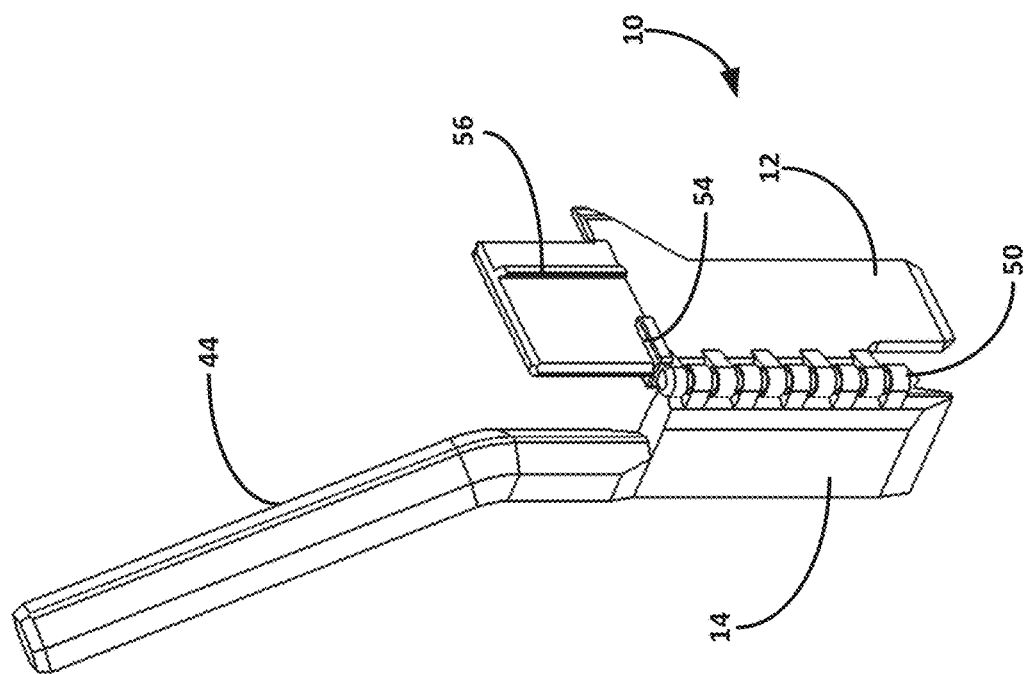
FIGS. 8A and 8B are front and rear perspective views, respectively, of an example configuration of a bi-planar instrument configured with a hinged connection.
Figure 8A:
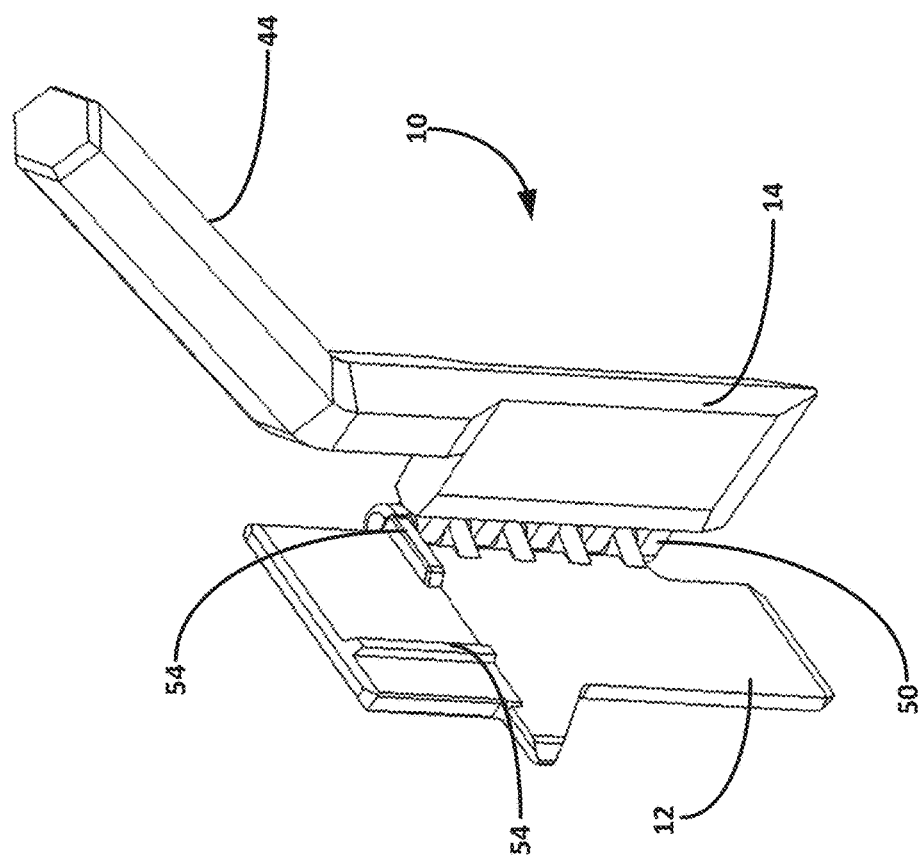

FIGS. 8A and 8B are front and rear perspective views, respectively, of an example configuration of bi-planar instrument 10 in which the instrument is configured with a hinged connection 50 between spacer body 12 and fulcrum body 14. In the illustrated configuration, spacer body 12 is directedly connected to fulcrum body 14 via hinge 50. In other implementations, spacer body 12 may be hingedly or fixedly connected to bridge member 16 which, in turn is connected to fulcrum body 14 with or without a hinged connection (e.g., a hinged connection or fixed connection). Configurating bi-planar instrument 10 with hinged connection 50 can be beneficial to allow spacer body 12 to rotate relative to fulcrum body 14, allowing the relative angle between the two components to be adjusted.

In use, the clinician can adjust the angle between spacer body 12 and fulcrum body 14 prior to, while, and/or after being inserting into joint spaces of a patient. This can allow the angle between spacer body 12 and fulcrum body 14 to be adjusted based on the needs of the condition being treated and/or specific anatomy of the patient undergoing the procedure. The clinician can rotate spacer body 12 and fulcrum body 14 relative to each other about hinge 50 prior to and/or after preparing one or both end faces of the bones defining a joint space into which spacer body 12 is to be inserted, as discussed above.

In some configurations, spacer body 12 and fulcrum body 14 can rotate relative to each other about an unbounded range from rotation (e.g., from a first position in which the inner face of spacer body 12 contacts the inner face of fulcrum body 14 to a second position in which the outer face of the spacer body contacts the outer face of the fulcrum body). In other configurations, spacer body 12 and fulcrum body 14 can rotate relative to each other within a bounded range of rotation. For example, bi-planar instrument 10 may include one or more rotation stops that limit the extent of rotation between spacer body 12 and fulcrum body 14.

Figure 9B:
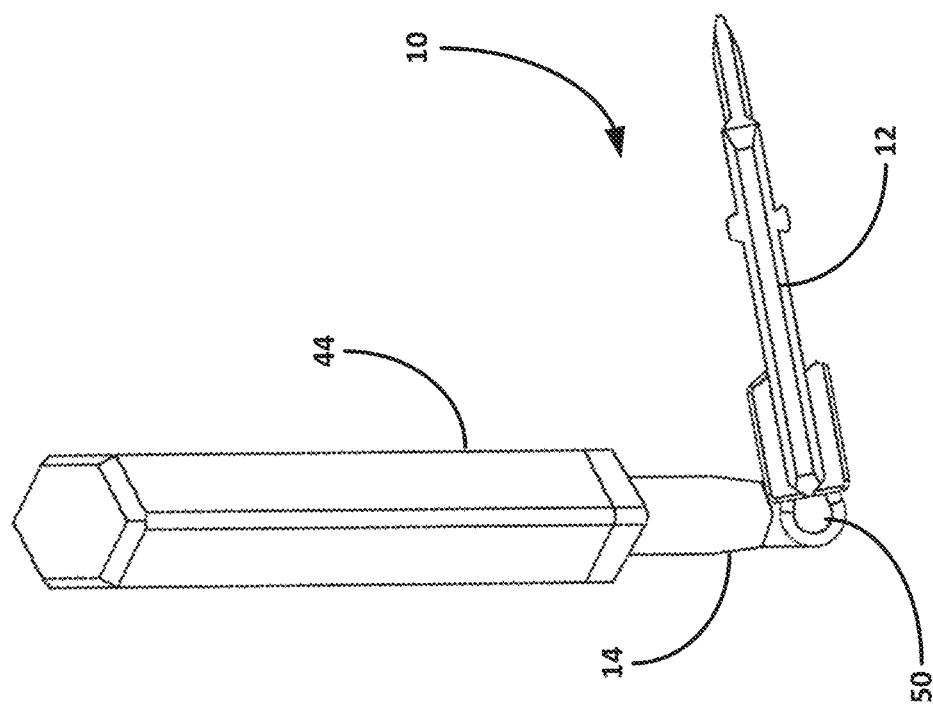
FIGS. 9A-9D illustrate example relative rotational positions between a spacer body and a fulcrum body for the example bi-planar instrument illustrated in FIGS. 8A and 8B.
Figure 9A:
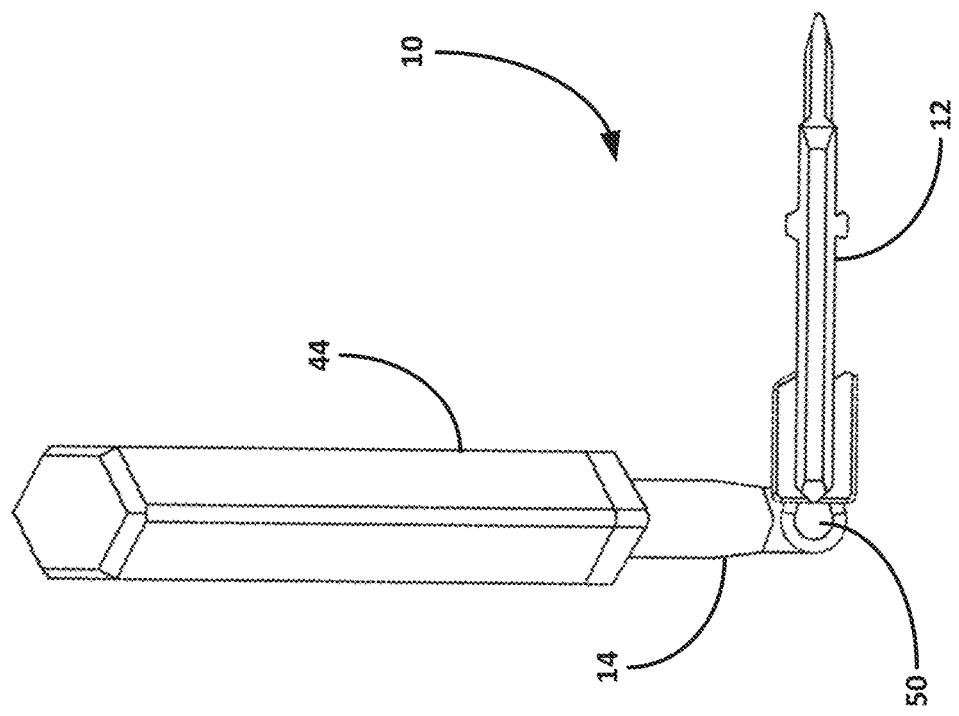
Figure 9D:
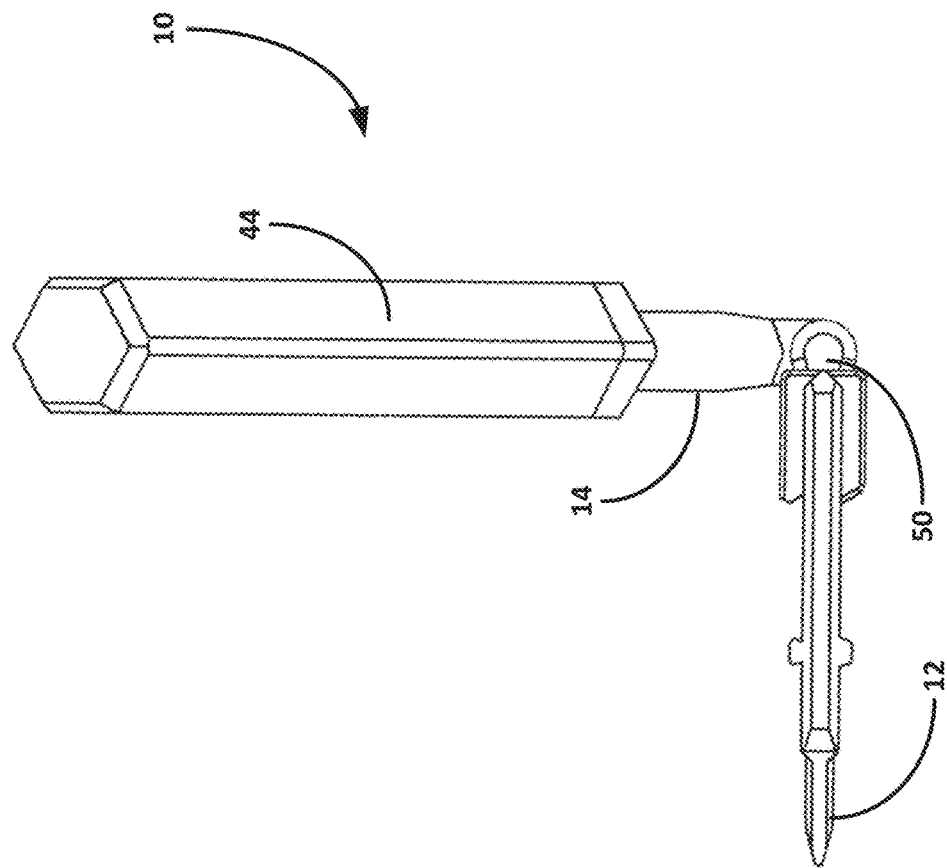
Figure 9C:
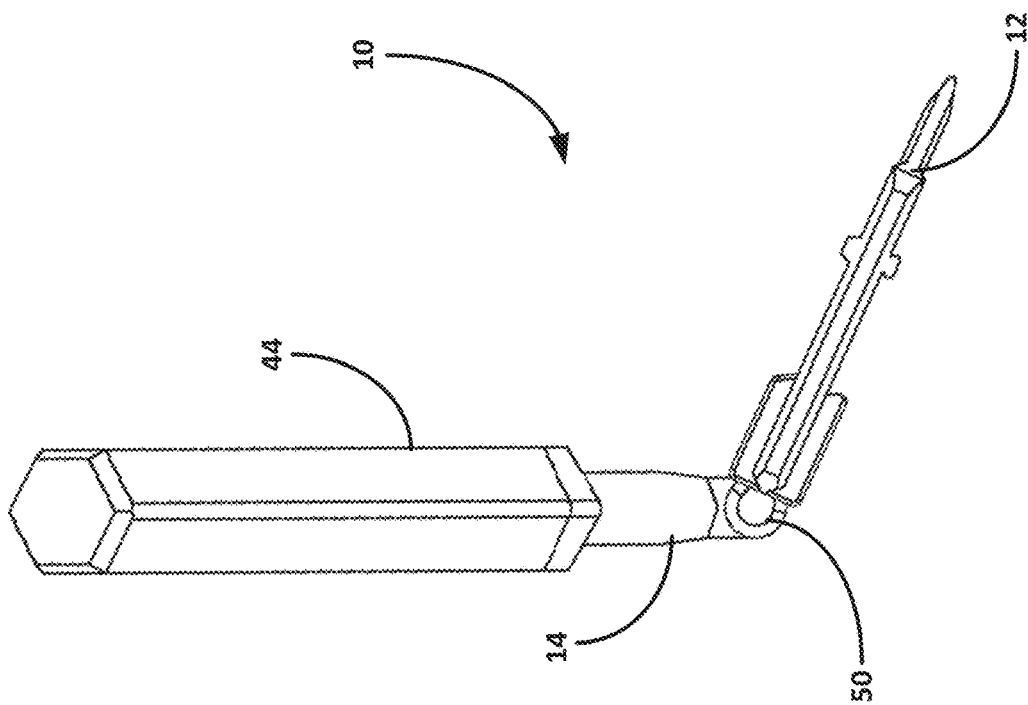

FIGS. 9A-9D illustrate example relative rotational positions between spacer body 12 and fulcrum body 14 of bi-planar instrument 10. FIG. 9A illustrates spacer body 12 extending perpendicularly (at a +90 degree angle) relative to fulcrum body 14. FIG. 9B illustrates spacer body 12 positioned at an acute angle with respect to fulcrum body 14. FIG. 9C illustrates spacer body 12 positioned at an obtuse angle relative to fulcrum body 14. Further, FIG. 9D illustrates spacer body 12 extending in an opposite perpendicular direction (at a −90 degree angle) relative to fulcrum body 14.

As shown in FIGS. 9A-9D, spacer body 12 may be configured to rotate through an arc of rotation greater 90 degrees, such as an arc of rotation of at least 180 degrees. For example, spacer body 12 may rotate relative to fulcrum body 14 about axis of rotation defined by hinge 50 from defining an angle of at least +45 degrees with respect to fulcrum body 14 to −45 degrees with respect to the fulcrum body. As a result, the position of spacer body 12 and fulcrum body 14 may be reversable. This can be useful to allow a single instrument 10 to be used on both the right foot and the left foot of a patient. The position of spacer body 12 can be rotated (e.g., approximately 180 degrees) depending on whether instrument 10 is intended to be used on a right foot or left foot.

As discussed above, bi-planar instrument 10 includes spacer body 12. Spacer body 12 can be sized and shaped to be positioned in a space between two bone portions, such as a joint space between adjacent bones (e.g., a TMT joint between a metatarsal and cuneiform). Spacer body 12 may include a first portion insertable into the space between adjacent bone portions and a second portion that projects above the space between the bone portions. The second portion projecting above the space can be coupled to a surgical instrument, such as a bone preparation guide, to control positioning of the surgical instrument over the bone portions defining the space into which spacer body 12 is inserted.

To engage the surgical instrument (which will subsequently be described with reference to bone preparation guide 30 for purposes of discussion) with spacer body 12, the surgical instrument can have a receiving opening configured to receive the portion of spacer body 12 projecting above the joint space into which the spacer body is inserted. Accordingly, the receiving opening and the spacer body can be sized and shaped relative to each other to allow the spacer body to be inserted into and/or through the receiving opening of the surgical instrument. In some configurations, the receiving opening of the surgical instrument is sized to conform to the size of the spacer body 12 to be inserted therein (e.g., such that there is little or no relative movement between the spacer body and surgical instrument, once the spacer body is inserted into the surgical instrument). In other configurations, the surgical instrument may be sized to allow relative movement between the spacer body and surgical instrument, even once the spacer body is inserted into the receiving opening of the surgical instrument.

Figure 10B:
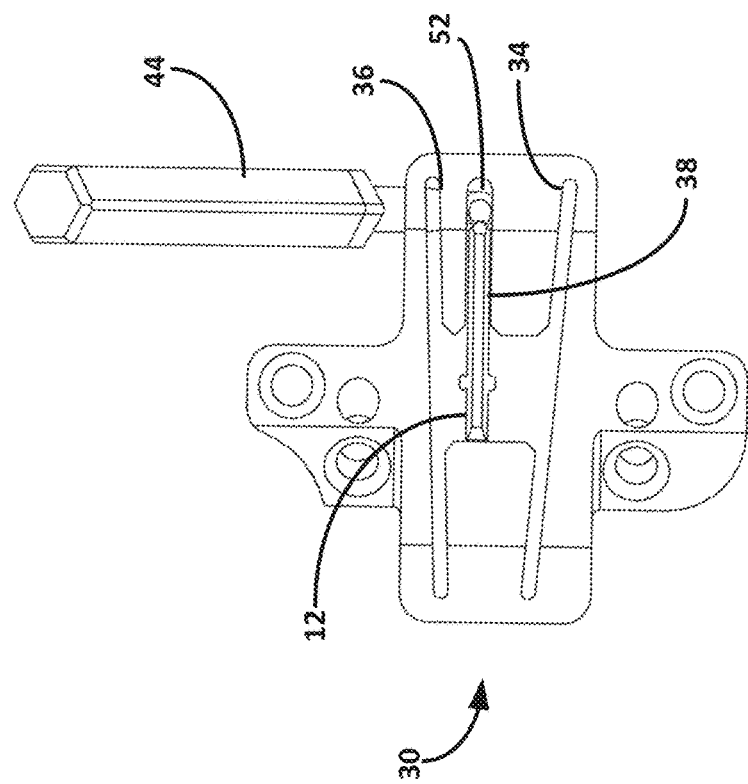
FIGS. 10A-10C are illustrations of an example system that includes a bi-planar instrument and a bone preparation guide, where the bone preparation guide is sized to move relative to the spacer body of the bi-planar instrument.
Figure 10A:
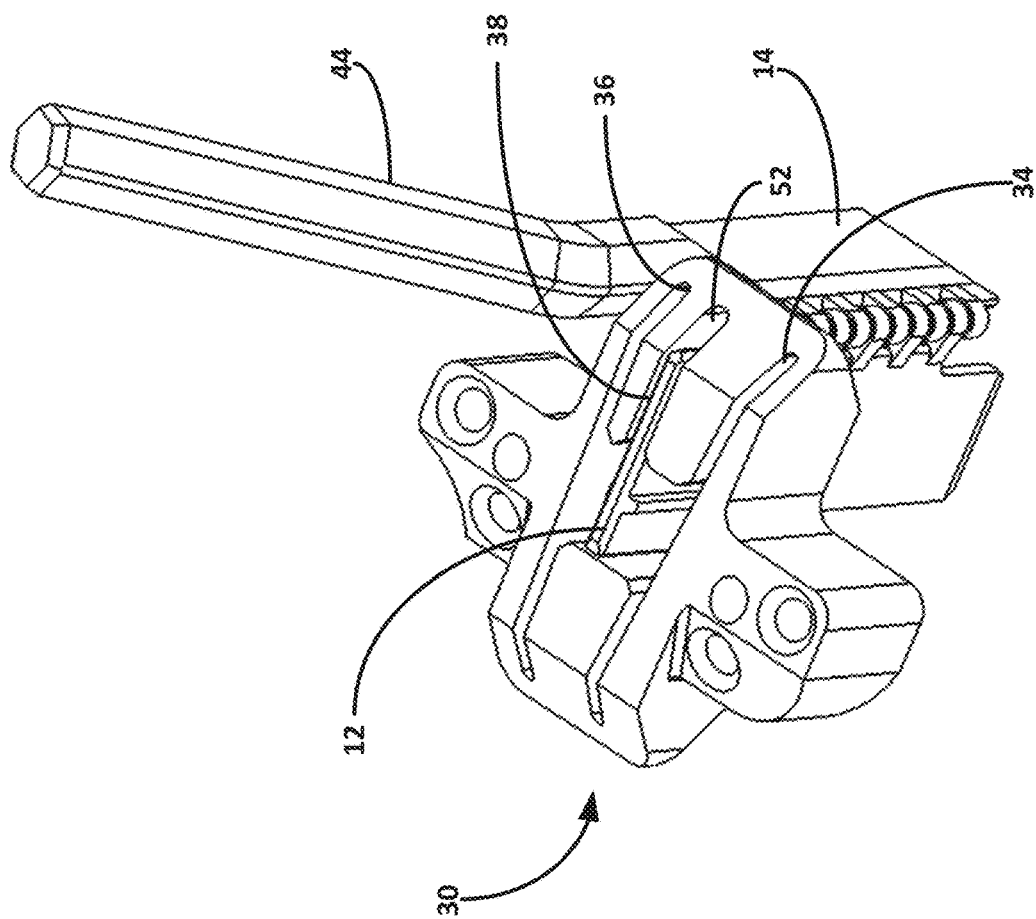
Figure 10C:
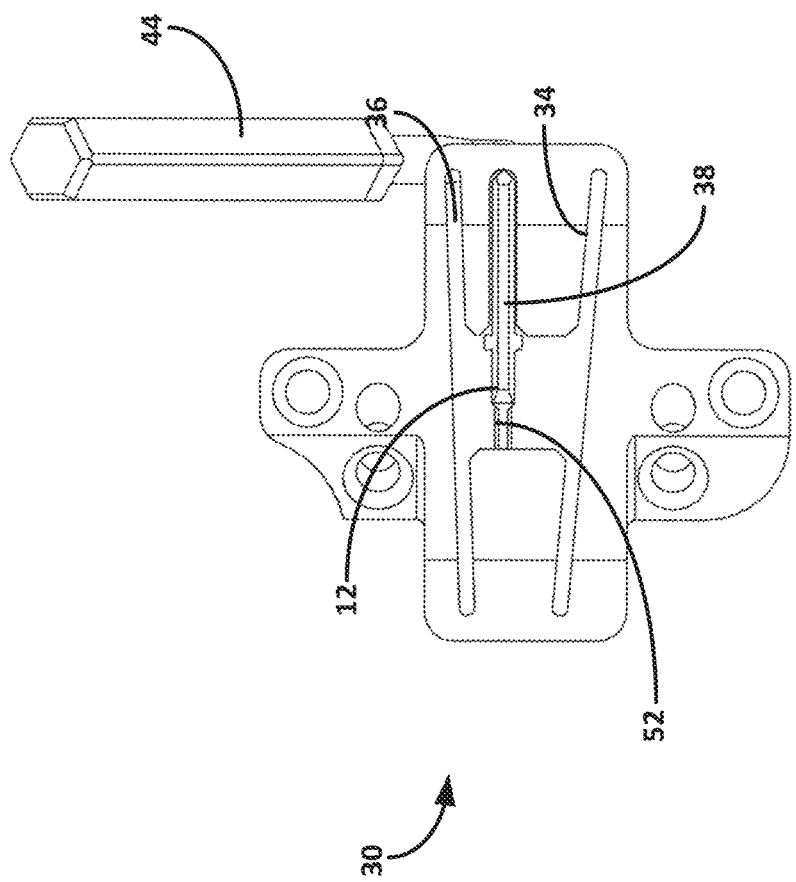

FIGS. 10A-10C are illustrations of an example system that includes bi-planar instrument 10 and bone preparation guide 30, where the bone preparation guide is configured to move relative to the spacer body of the bi-planar instrument. FIGS. 10A and 10B are perspective and top views, respectively, showing the spacer body 12 of bi-planar instrument 10 inserted into receiving opening 38 of bone preparation guide 30 at a first position. FIG. 10C is a top view showing the spacer body 12 of bi-planar instrument 10 inserted into receiving opening 38 of bone preparation guide 30 at a second position, which is moved in the transverse plane relative to the first position.

As shown in the examples of FIGS. 10A-10C, opening 38 of bone preparation guide 30 is sized is larger than the portion of spacer body 12 received in the opening in one or more dimensions (e.g., only one). In particular, in the illustrated example, opening 38 of bone preparation guide 30 is sized to facilitate linear movement of bone preparation guide 30 relative to spacer body 12 in the transverse plane, e.g., when installed over a TMT joint. Opening 38 of bone preparation guide 30 has a region 52 that is longer than a length of spacer body 12 inserted into the opening. As a result, bone preparation guide 30 can slide relative to spacer body 12, while the spacer body projects upward through the opening. This can be useful to allow the clinician to reposition one or more guide surfaces 34, 36 of the bone preparation guide relative to one or more bone ends to be prepared, even once the bone preparation guide is installed on the spacer body inserted into the joint space.

FIGS. 10A and 10B illustrate bone preparation guide 30 translated to a lateral-most extent (when positioned on a foot), such that the region 52 of opening 38 that is larger than spacer body 12 is located on the lateral side of the spacer body. FIG. 10C illustrates bone preparation guide 30 translated to a medial-most extent (when positioned on a foot), such that the region 52 of opening 38 that is larger than spacer body 12 is located on the medial side of the spacer body. The clinician can also move bone preparation guide 30 to one or more intermediate positions in the region 52 of opening 38 that is larger than spacer body 12 is split between the medial and lateral sides of spacer body 12.

In some configurations, opening 38 is sized relative to the size of spacer body 12 such that the bone preparation guide can translate a distance of at least 0.5 mm relative to spacer body 12, such as at least 1 mm, at least 2 mm, or at least 5 mm. For example, opening 38 may be sized relative to the portion of spacer body 12 to be received therein to be from 0.5 mm to 25 mm longer than a length of the spacer body, such as from 1 mm to 10 mm longer. This can allow from 0.5 mm to 25 mm of relative movement between the bone preparation guide and spacer body, such as from 1 mm to 10 mm of relative movement. When bone preparation guide 30 is installed over a TMT joint, the bone preparation guide can be moved relative to spacer body 12 in the transverse plane (in a medial to lateral direction) utilizing the extra length of opening 38 relative to the size of the spacer body.

In some examples, opening 38 of bone preparation guide 30 is configured (e.g., sized and/or shaped) relative to spacer body 12 to allow relative movement between the bone preparation guide and spacer body in the frontal plane and/or sagittal plane, in addition to or in lieu of allowing relative movement in the transverse plane. In other examples, spacer body 12 and bone preparation guide 30 are configured to inhibit movement relative to each other in one or more planes. Spacer body 12 and bone preparation guide 30 may be configured to inhibit movement relative to each other in one or more planes by sizing and/or shaping the two features relative to each other to prevent or restrict movement in the one or more planes.

With further reference to FIGS. 8A and 8B, bi-planar instrument 10 is illustrated as including a shelf 54 projecting outwardly from a remainder of spacer body 12. Shelf 54 may be a region of increased thickness relative to the remainder of spacer body 12. Shelf 54 may extend outwardly from a remainder of spacer body 12 from one side of the spacer body (e.g., a front face) or multiple sides of the spacer body (e.g., a front face and a rear face), as illustrated in the examples of FIGS. 8A and 8B. Shelf 54 may be located above the portion of spacer body that is insertable into the joint space between adjacent bones. In other words, shelf 54 may be located on the portion of spacer body 12 that is insertable into opening 38 of bone preparation guide 30. By configuring spacer body 12 with shelf 54, the increased thickness of spacer body 12 in the region of shelf 54 may prevent or eliminate relative movement between the spacer body and bone preparation guide in the frontal and/or sagittal planes (when installed on a foot). As a result, bone preparation guide 30 may translate relative to spacer body 12 in a transverse plane direction but may be in a substantially fixed orientation relative to the spacer body in the frontal and/or sagittal planes.

In the illustrated example of FIGS. 8A and 8B, bi-planar instrument 10 is also illustrated as having a protrusion 56 extending outwardly from one or both faces of spacer body 12. Protrusion 56 can form a bullseye (e.g., an X or T-shaped intersection) when viewing spacer body 12 from above. This can be useful when visualizing spacer body 12 under fluoroscopy to help the clinician interpret where the spacer body is located in the joint space and/or relative to bone preparation guide 30.

While bi-planar instrument 10 has generally been described as being useful for insertion into a space between opposed bone ends transitioning into an intermetatarsal space, the instrument may be used in any desired application and the disclosure is not limited in this respect. For example, bi-planar instrument 10 may be positioned between different bone portions and/or inserted into different joint space(s) than those expressly discussed above. Further, while bi-planar instrument 10 has generally been described with spacer body 12 configured to be positioned in a first joint space and fulcrum body 14 configured to be positioned in second joint space intersecting with and angled relative to the first joint space, the bi-planar instrument can be used with only one of spacer body 12 and fulcrum body 14 positioned in a joint space (and/or positioned between different bone portions).

As one example application, bi-planar instrument 10 may be utilized in a total ankle replacement procedure. One body (e.g., spacer body 12 or fulcrum body 14) can be inserted between the talus and the tibia in the coronal plane and parallel to the frontal plane. The other body can be inserted between the tibia and the talus in the sagittal plane on the medial side or between the fibula and the talus on the lateral side.

As another example application, bi-planar instrument 10 can be utilized in a total knee replacement procedure. One body (e.g., spacer body 12 or fulcrum body 14) can be inserted between the tibia and femur and the other body positioned around either the medial or lateral condyle of the femur or the tibial plateau of the tibia to align a cut guide with the axis of the femur or tibia.

As still a further example application, bi-planar instrument 10 can be utilized in a total elbow replacement procedure. One body (e.g., spacer body 12 or fulcrum body 14) can be inserted between the ulna and humerus for either an ulnar or radial resection. The other body can be positioned around either the medial or lateral side of the bone (ulna or humerus) to set an angle of cut on either bone.

Various examples have been described. These and other examples are within the scope of the following claims.

The invention claimed is:

1. A method for correcting an alignment of a bone in a foot and preparing bones for fusion, the method comprising:
   inserting a unitary instrument comprising a spacer body connected to a fulcrum body between bones of a foot by inserting the spacer body into a joint space between a metatarsal and an opposed cuneiform and simultaneously inserting the fulcrum body between the metatarsal and an adjacent metatarsal,
   preparing an end of the metatarsal using a bone preparation guide aligned with the spacer body to guide a bone preparation instrument;
   preparing an end of the opposed cuneiform using the bone preparation guide to guide the bone preparation instrument; and
   moving the metatarsal relative to the adjacent metatarsal in at least a transverse plane, thereby pivoting the metatarsal about the fulcrum body and reducing an intermetatarsal angle between the metatarsal and the adjacent metatarsal.

2. The method of claim 1, wherein the spacer body is connected to the fulcrum body with a bridge member.

3. The method of claim 2, wherein inserting the unitary instrument comprises positioning the bridge member against a proximal-lateral corner of the metatarsal.

4. The method of claim 1, wherein the spacer body is fixedly connected to the fulcrum body.

5. The method of claim 1, wherein an angle defined between the spacer body and fulcrum body is within a range from 60 degrees to 120 degrees.

6. The method of claim 1, further comprising adjusting an angle defined between the spacer body and fulcrum body.

7. The method of claim 6, wherein the spacer body is hingedly attached to the fulcrum body, and adjusting the angle defined between the spacer body and fulcrum body comprises rotating the spacer body relative to the fulcrum body about a hinged connection.

8. The method of claim 6, wherein adjusting the angle defined between the spacer body and fulcrum body comprises bending a malleable section of material connecting the spacer body to the fulcrum body.

9. The method of claim 1, wherein inserting the spacer body into the joint space comprises inserting a first portion of the spacer body into the joint space with a second portion of the spacer body extending above the joint space, and further comprising aligning the bone preparation guide with the second portion of the spacer body.

10. The method of claim 9, wherein the second portion of the spacer body is sized smaller than a receiving opening of the bone preparation guide into which the second portion of the spacer body is inserted, and further comprising moving the bone preparation guide in at least one plane relative to the spacer body, with the spacer body inserted into the receiving opening.

11. The method of claim 10, wherein the second portion of the spacer body further comprises a shelf extending outwardly from at least one a front face and a rear face of the spacer body, the shelf restricting movement between the bone preparation guide and the spacer body.

12. The method of claim 1, wherein the bone preparation guide is permanently connected to the spacer body, and inserting the spacer body into the joint space comprises positioning the bone preparation guide over the metatarsal and the opposed cuneiform.

13. The method of claim 1, further comprising a handle projecting at a non-zero degree angle away from the fulcrum body, wherein inserting the fulcrum body further comprises retracting tissue laterally away from an incision providing access to the metatarsal and the adjacent metatarsal and holding the tissue away from the incision in a tissue retraction space formed between the handle and the fulcrum body.

14. The method of claim 1, wherein:
the metatarsal is a first metatarsal,
the opposed cuneiform is a medial cuneiform, and
the adjacent metatarsal is a second metatarsal.

15. The method of claim 1, further comprising removing at least the spacer body from the joint space, compressing a prepared end of the metatarsal against a prepared end of the opposed cuneiform, and fixating the prepared end of the metatarsal to the prepared end of the opposed cuneiform.

16. The method of claim 15, wherein removing at least the spacer body further comprises removing the fulcrum body connected to the spacer body.

17. The method of claim 15, wherein fixating the prepared end of the metatarsal to the prepared end of the opposed cuneiform comprises inserting a fixation member across a tarsometatarsal joint.

18. The method of claim 1, wherein preparing the end of the metatarsal and preparing the end of the opposing cuneiform comprises preparing one or both of the end of the metatarsal and the end of the opposing cuneiform after moving the metatarsal relative to the adjacent metatarsal.

19. The method of claim 1, further comprising applying at least one fixation device across the joint space between a prepared end of the metatarsal and a prepared end of the opposed cuneiform.

20. The method of claim 19, wherein the at least one fixation device comprises a bone plate.

21. The method of claim 1, wherein the spacer body and fulcrum body are fabricated as separate components that are subsequently connected together to form the unitary instrument.

* * * * *